(12) United States Patent
Isacson et al.

(10) Patent No.: US 8,545,834 B2
(45) Date of Patent: Oct. 1, 2013

(54) G-SUBSTRATE FOR THE TREATMENT AND PREVENTION OF PARKINSON'S DISEASE

(75) Inventors: Ole Isacson, Cambridge, MA (US); Chee-Yeun Chung, Cambridge, MA (US)

(73) Assignee: The McLean Hospital Corporation, Belmont, MA (US)

( * ) Notice: Subject to any disclaimer, the term of this patent is extended or adjusted under 35 U.S.C. 154(b) by 736 days.

(21) Appl. No.: 12/531,044

(22) PCT Filed: Mar. 11, 2008

(86) PCT No.: PCT/US2008/056533
§ 371 (c)(1),
(2), (4) Date: Mar. 22, 2010

(87) PCT Pub. No.: WO2008/112701
PCT Pub. Date: Sep. 18, 2008

(65) Prior Publication Data
US 2010/0203111 A1 Aug. 12, 2010

Related U.S. Application Data

(60) Provisional application No. 60/895,074, filed on Mar. 15, 2007.

(51) Int. Cl.
*A01N 63/00* (2006.01)
*A61K 48/00* (2006.01)

(52) U.S. Cl.
USPC ...................................... 424/93.2; 514/44 R

(58) Field of Classification Search
None
See application file for complete search history.

(56) References Cited

U.S. PATENT DOCUMENTS

| 5,487,739 | A | 1/1996 | Aebischer et al. |
| 5,595,760 | A | 1/1997 | Cherif-Cheikh |
| 5,639,275 | A | 6/1997 | Baetge et al. |
| 5,653,975 | A | 8/1997 | Baetge et al. |
| 5,672,659 | A | 9/1997 | Shalaby et al. |
| 6,027,721 | A | 2/2000 | Hammang et al. |
| 6,080,728 | A | 6/2000 | Mixson |
| 2006/0204519 | A1 | 9/2006 | Johnson |
| 2006/0233766 | A1 | 10/2006 | Messina et al. |

FOREIGN PATENT DOCUMENTS

WO WO-97/44065 11/1997

OTHER PUBLICATIONS

Aswad et al, A Specific Substrate from Rabbit Cerebellum for Guanosine 3':5'-Monophosphate-dependent Protein Kinase, J. Biol. Chem., 256(7):3487-3493, 1981.
Aswad et al, A Specific Substrate from Rabbit Cerebellum for Guanosine 3':5'-Monophosphate-dependent Protein Kinase, J. Biol. Chem., 256(7):3494-3500, 1981.
Chatfield et al., Inhibitors of protein phosphatases 1 and 2A differentially prevent intrinsic and extrinsic apoptosis pathways, Biochem. Biophys. Res. Commun. 323: 1313-1320, 2004.
Chen et al., Glycogen synthase kinase 3β (GSKβ) meidates 6-hydroxydopamine-induced neuronal death, FASEB J. 18: 1162-1164, 2004.
Choi et al, Phosphoylation of p38 MAPK Inducted by Oxidative Stress is Linked to Activation of both Caspase-9- and -9-mediated Apoptotic Pathways in Dopaminergic Neurons, J. Biol. Chem., 279:20451-20460, 2004.
Chung et al, Cell type-specific gene expression of midbrain dopaminergic neurons reveals molecules involved in their vulnerability and protection, Hum. Molec. Gen., 2005, vol. 14, No. 13, pp. 1709-1725.
Endo et al, Molecular identification of human G-substrate, a possible downstream component of the cGMP-dependent protein kinase cascade in cerebellar Purkinje cells, Proc. Natl. Acad. Sci., USA, 96:2467-2472, 1999.
Endo et al., Thr123 of rat G-substrate contributes to its action as a protein phosphatase inhibitor, Neurosci. Res. 45: 79-89, 2003.
Garcia et al, Serine/threonine protein phosphatases PP1 and PP2 are key players in apoptosis, Biochimie 85: 721-726, 2003.
Gardlik et al, Vectors and delivery systems in gene therapy, Med. Sci. Monit, 11(4):RA110-121, 2005.
Greene et al, Gene expression profiling of rat midbrain dopamine neurons: implications for selective vulnerability in parkinsonism, Neurobiology of Disease, 2005, vol. 18, pp. 19-31.
Grimm et al, Molecular basis for catecholaminergic neuron diversity, Proc. Natl. Acad. Sci. USA, Sep. 21, 2004, vol. 101, No. 38, pp. 13891-13896.
Hall et al, Phosphorylation-dependence Inhibition of Protein Phosphatase-1 by G-substrate, J. Biol. Chem, 274(6): 3485-3495, 1999.
International Search Report dated Sep. 18, 2008 for PCT Application No. PCT/US08/056533.
Janssens et al, Protein phosphatase 2A: a highly regulated family of serine/threonine phosphatases implicated in cell growth and signalling, Biochem. J., 353:417-439, 2001.
Kennedy, P., Potential use of herpes simplex virus (HSV) vectors for gene therapy of neurological disorders, Brain, 120:1245-1259, 1997.
Lee et al, Novel molecular approaches to cystic fibrosis gene therapy, Biochem. J., 387:1-15, 2005.
Moreau-Gaudry et al, High-level erythroid-specfic gene expression in primary human and murine hematopoietic cells with self-inactivating lentiviral vectors, Blood, 98:2664-2672, 2001.
Morelli et al, Neuronal and glial cell type-specific promoters within adenovirus recombinants restrict the expression of the apoptosis-inducing molecule Fas ligand to predetermined brain cell types, and abolish peripheral liver toxicity, J. Gen. Virol, 80:571-583, 1999.
Nabel et al., Recombinant Gene Expression in Vivo Within Endotheilial Cells of the Arterial Wall, Science, 244:1342-1344, 1989.
Ou et al, Monoamine oxidase A and repressor R1 are involved in apoptotic signaling pathway, Proc. Natl, Acad. Sci. USA, 103:10923-10928, 2006.
Ray et al, Protein Phosphatase 2A Regulates Apoptosis in Intestinal Epithelial Cells, J. Biol. Chem, 280(35):31091-31100, 2005.

(Continued)

Primary Examiner — Anne-Marie Falk
(74) *Attorney, Agent, or Firm* — Nixon Peabody LLP; David S. Resnick; Leena H. Karttunen Contarino

(57) ABSTRACT

The invention features methods and compositions for the treatment and prevention of Parkinson's Disease.

6 Claims, 17 Drawing Sheets

(56) References Cited

OTHER PUBLICATIONS

Romano et al, Latest Developments in Gene Transfer Technology: Achievements, Perspectives, and Controversies over Therapeutic Applications, Stem Cells, 18:19-39, 2000.

Ruano et al., Role of p28 and Inducible Nitric Oxide Synthase In The in Vivo Dopaminergic Cells' Degeneration Induced by Inflammatory Processes After Lipopolysaccharide Injection, Neurosci. 140: 1157-1168, 2006.

Song et al., The activation of Akt/PKB signaling pathway and cell survival, J. Cell. Mol. Med. 9: 59-71, 2005.

Swingle et al. Small Molecule Inhibitors of Ser/thr Protein Phosphatases: Specificity, Use and Common Forms of Abuse, Methods Mol. Biol. 365: 23-38, 2006.

Tamura et al., The phosphorylation status and anti-apoptotic activity of Bcl-2 are regulated by ERK and protein phosphatase 2A on the mitochondria, FEBS Lett. 569: 249-255, 2004.

Chung et al., Abstract from Society for Neuroscience, presentation Oct. 18, 2006. "Elevated expression of G-substrate in A10 dopaminergic neurons may contribute to their decreased vulnerability in Parkinson's Disease.".

FIGURE 5A

```
1    MMSTEQMQPL EVSEDRLDKL DPRCSHLDDL SDQFIKDCDL KKKPRKGKNV   50
51   QATLNVESDQ KKPRRKDTPA LHIPPFIPGV FSEHLIKRYD VQERHPKGKM  100
101  IPVLHNTDLE QKKPRRKDTP ALHMSPFAAG VTLLRDERPK AIVEDDEKDG  150
151  DKIAI                                                  155
(SEQ ID. NO: 1)
```

FIGURE 5B

```
1    GGAGGGCGCT GATTGTGCTG GAGAAGAAAT ACATCCACCC ACCCTCCTTT GATGATGTCC
61   ACTGAGCAAA TGCAGCCACT GGAAGTCTCA GAAGACAGAC TGGACAAGCT AGACCCTCGT
121  TGCAGCCACT TAGATGATCT TTCAGACCAG TTCATTAAGG ACTGTGATCT CAAAAAGAAG
181  CCTAGAAAGG GAAAAAATGT ACAGGCACCC CTGAATGTTG AGTCAGACCA AAAAAAACCA
241  AGGAGGAAAG ATACACCGGC GCTGCACATC CCACCTTTCA TACCAGGTGT GTTTTCAGAA
301  CATTTAATTA AAAGATACGA TGTTCAAGAG AGACATCCAA AGGGCAAAAT GATCCCTGTT
361  CTTCATAACA CTGACCTGGA ACAGAAAAAG CCAAGGAGAA AGACACACC TGCCCTGCAC
421  ATGTCCCCCT TTGCAGCAGG TGTGACATTG CTCAGGGATG AGAGACCCAA AGCAATCGTG
481  GAAGATGACG AAAAGGATGG TGACAAGATA GCTATTTAAA GATAGTTTCC CTGAGACCAC
541  TTGTAAATAG GTTAGATTGG TTCCCTGTGG TGACCTAGAG AAAAAATAGA CTTGTTTCTG
601  CTCTCATTTT TGTCATCGTC TGACTTGAAG ATTCAGACAC CTTCTCCCCA GGAGATGTAT
661  GCCATCAAAT TGCCAGTCAC CTCTTTGTCT CTCTCTTCTT TCTGAGTATG GTTTCTATTC
721  TGTGTTTTGA ATTTTTATTT TCTAATGCAG TGGAAAAGAA ACAGATCATC CTAAATGAGG
781  AGGTAACAGG GAAAGCACTG GGGTCGGTT TCTGCATCTT CTGGATCAAT TCACGGAACA
841  GAGATCGTGG ATTACATGGG CTCCTTCTTG GTTTTGCTG CTGGGCAGGA CTTGACTTAG
901  CATTATCCAA GCACCAGTCC AAGTGGGGTT CCCTGTTGCC AGTTAGAGAG GTGAGAATGT
961  TTGGACTCTA ACTCACCGAT TGCTTTGCAG ACAAAGGTCT TTTATTTCTC CTGTCCTATC
1021 TTAAGAGTCC AAATGTCTCT GGTGATGTTC CTAAGACCCT TGTCCCAGAT ACTCTAAATG
1081 TGAATGTATG AGCTGGGGGA GTCAACCCAG CCCACCATGC GTTGGCTGAT GATACCAGAG
1141 GCAGAGAGTG CTGGTCTGTC TGGGAAGCTT AGCAATGTAT CTTCAAATTT ATTTTTGTTT
1201 TTAAAAATAT TTCTTAAACA TGCTGTCCCA ACATTTGTGA GTTGTGTCAC AAGTGAGTCA
1261 TTATCAATGG TAGATAAAAT ATCAATGTTT GTGATGAATT TACTGTAAAA AAATTAAGGT
1321 CAATGAAAGC CATTCTGTTA TTTTTAGCAT TCTCACTTAT TTAGACTCTA TTACACTTTC
1381 TTGGATGAGA GGGGAGAGTG TGGTGTTAGC TAGTGAGCAG AGGTCTGTAT ATTGTCCTTG
1441 CCCCAGCCTG CAATCTGTGG ATGCCCAGGG GAAGGCATAC AGGCCTCATC CACCAGGCAA
1501 TAGACAGGAG AGAGGTGAGA ACTATTTTTA GAAGGAGGAA AAGTAGATAC GCAAATTGTC
1561 ACAACTAAGA GTGATAATTT GGTAGCTCTG TATGTATGCT GGTTCCAACT GTTTAATCCC
1621 TTCTGTCTTT CTGTTCTCAC AAAGATGGAA AAGATGCAAG AGCTTGCCGG AAATAAAGCT
1681 ACATCTATCC
(SEQ ID. NO: 2)
```

FIGURE 5C

```
1    MSTEMMTTEP VQSLELSEDI LDKLDPHGSH SDDLSDQFIK DCDLKKKPRK   50
51   GKNVQATLNV ESDQKKPRRK DTPALHIPPF IPGVISEHLI KRYDVQERIP  100
101  KGKTGPALHN TDVEQKRPRR KDTPAFHVPP FVAGLTLLED EGTGVIMEDE  150
151  EMDGDKLAI                                              159
(SEQ ID. NO: 3)
```

G-SUBSTRATE FOR THE TREATMENT AND PREVENTION OF PARKINSON'S DISEASE

CROSS-REFERENCE TO RELATED APPLICATIONS

This application is the U.S. National Phase of PCT Application No. PCT/US2008/056533 filed on Mar. 11, 2008 which claims priority to U.S. Provisional Application No. 60/895,074 filed on Mar. 15, 2007, all of which are fully incorporated herein by reference.

GOVERNMENT SUPPORT

This invention was made with Government support under Grant No. NS039793 awarded by the National Institutes of Health. The Government has certain rights in this invention.

SEQUENCE LISTING

The instant application contains a Sequence Listing which has been submitted in ASCII format via EFS-Web and is hereby incorporated by reference in its entirety. Said ASCII copy, created on Apr. 18, 2013, is named 063476-073802_SL.txt and is 6,973 bytes in size.

BACKGROUND OF THE INVENTION

This invention relates generally to the diagnosis and treatment of neurodegenerative diseases, including Parkinson's Disease.

Parkinson's disease (PD) is a progressive neurodegenerative disease characterized clinically by bradykinesia, rigidity, and resting tremor. Selective degeneration of specific neuronal populations is a universal feature of PD that contributes to the clinical symptomology which is poorly understood. The hallmark neuropathologic feature of PD is loss of midbrain DA neurons. While the majority of PD cases are sporadic, for which a combination of environmental and genetic factors are likely responsible, familial cases that result from monogenic mutations have also been identified in genes including α-synuclein, parkin, ubiquitin C-terminal hydrolase-1, DJ-1, PINK1, and LRRK2. Regardless of specific etiology, DA neurons in the A9 region (substantia nigra pars compacta; SNc) are considerably more vulnerable than DA neurons in the immediately adjacent A10 region (ventral tegmental area; VTA) 3,4. A similar pattern of differential vulnerability is observed in rodent and primate models of PD, including toxic models utilizing 6-hydroxydopamine (6-OHDA) 5 and 1-methyl 4-phenyl 1,2,3,6-tetrahydropyridine (MPTP), indicating that such differential vulnerability between A9 and A10 DA neuronal populations may be conserved between species.

It has recently been demonstrated that rodent A9 and A10 DA neurons have distinct gene expression profiles despite their many similarities (Grimm et al., Proc. Natl. Acad. Sci. USA 101: 13891-13896, 2004; Chung et al., Hum. Mol. Genet. 14: 1709-1725, 2005; Greene et al., Neurobiol. Dis. 18: 19-31, 2005). Such inherent baseline gene expression differences may create biochemical identities that underlie the different thresholds of vulnerability to pathophysiological processes. Indeed, it was recently shown that altering expression of several differentially expressed genes in cell culture did affect the vulnerability to neurotoxins (Chung et al., 2005).

Currently, little is known about the mechanism underlying the neurodegenerative process and the basis for its differential effects on the A9 versus the A10 dopaminergic neurons. Accordingly, disease management is largely limited to strategies that achieve symptomatic relief (e.g., by replenishing dopamine levels) rather than strategies that seek to prevent or delay neurodegeneration. Thus, better treatment methods are needed for treating and preventing neurodegenerative disorders that address the underlying molecular etiology of the disease.

SUMMARY OF THE INVENTION

This invention features a method for treating or preventing Parkinson's Disease (PD) in a patient by increasing the level of G-substrate or a biologically active fragment thereof, in the midbrain of that patient. In one embodiment, the level of G-substrate is increased in the midbrain dopaminergic neurons including, for example, the A9 (substantia nigra) and/or A10 (ventral tegmental area) dopaminergic neurons. The G-substrate levels may be increased using a vector comprising a polynucleotide encoding the G-substrate protein or biologically active fragment thereof, operably linked to a promoter, wherein the vector is taken up by the target cell (e.g., neuron or pluripotent stem cell) and the polynucleotide (and G-substrate protein) is expressed. In some embodiments, the vector is a viral vector including, for example, an adenovirus, adeno-associated virus, retrovirus, or lentivirus. The vector may be delivered to the midbrain in vivo using any suitable technique including, for example, stereotactic microinjection of the vector into or near the substantia nigra. The delivery method is designed to promote uptake and expression of the vector by the dopaminergic neurons.

In another aspect, the invention features a method for treating or preventing PD in a patient by increasing the level of Akt phosphorylation in the midbrain dopaminergic neurons of the patient. The level of Akt phosphorylation may be increased by increasing the expression level or biological activity of G-substrate or by reducing the expression level or inhibiting the enzymatic activity of protein phosphatase 2A (PP2A). Known PP2A inhibitors include, for example, cantharidin and calyculin A (reviewed in, for example, Swingle et al. Methods Mol. Biol. 365: 23-38, 2006).

In another aspect, the invention features a method for treating or preventing PD in a patient by inhibiting PP2A biological activity in the midbrain dopaminergic neurons of the patient. PP2A biological activity may be reduced by inhibiting expression of PP2A or inhibiting enzymatic activity.

In another aspect, the invention features a method for treating or preventing PD in a patient by administering to the patient a G-substrate protein or biologically active fragment thereof. In some embodiments, the G-substrate protein is administered by intravenous or intraventricular injection. The G-substrate protein may be soluble or may be encapsulated within a liposome. Alternatively, the G-substrate protein is administered to the brain of the patient by implanting cells capable of expressing a recombinant G-substrate protein. In one embodiment, the cells are autologous and are transplanted directly into the midbrain of the patient. Alternatively, the cells are derived from pluripotent stem cells, including umbilical cord blood stem cells, neuronal progenitor cells, fetal mesencephalic cells, embryonic stem cells, and postpartum derived cells (U.S. Pat. No. 5,487,739). In another embodiment, the transplanted cells are encapsulated in a permeable capsule.

In another aspect, the invention features a method for inhibiting PP2A activity in an individual in need thereof. In one embodiment, the individual is diagnosed as having Parkinson's disease, or is at risk of developing Parkinson's disease. In preferred embodiments, PP2A activity is inhibited by administering to the individual a PP2A inhibitor (e.g., cantharidin and calyculin A), G-substrate or a biologically active fragment thereof, or a vector encoding G-substrate or a biologically active fragment thereof.

In another aspect, the invention provides an isolated nucleic acid comprising a nucleotide sequence that encodes a G-substrate protein or biologically active fragment thereof and a promoter. In some embodiments, the promoter is a neuron-specific promoter including, for example, a neuron-specific enolase promoter or a synapsin-I promoter. In a related aspect, the invention provides vectors comprising such isolated nucleic acids. The vectors may be a naked DNA or a viral vector including, for example, those selected from the group of adenovirus, adeno-associated virus, retrovirus, lentivirus, and herpes simplex virus. The vectors are preferably contained in a pharmaceutically acceptable formulation including, for example, a formulation suitable for intravenous, intramuscular, intracerberoventricular, or intranigral injection. In another related aspect, the invention provides cells containing such isolated nucleic acids or vectors. In some embodiments, the cells include, for example, pluripotent stem cells, umbilical cord blood stem cells, neuronal progenitor cells, fetal mesencephalic cells, embryonic stem cells, and postpartum derived cells.

By "G-substrate" is meant a protein having an amino acid sequence substantially identical to the sequence of SEQ ID NO.: 1 or 3, and biologically active fragments thereof. A cDNA encoding G-substrate has the nucleic acid sequence of SEQ ID NO.: 2 (Hall et al., 1999) and GenBank Accession No. AF071789.

By "human G-substrate" is meant a protein having an amino acid sequence substantially identical to the sequence of SEQ ID NO.: 3, and biologically active fragments thereof.

By "biologically active G-substrate fragment" is meant any protein or polypeptide that is substantially identical to a portion of SEQ ID NOs: 1 or 3 and possesses at least one biological activity of G-substrate. In preferred embodiments, the G-substrate fragment contains at least one (and preferably both) threonine residues corresponding to Thr72 and Thr123 of the rat G-substrate provided in SEQ ID NO.: 3 (Thr68 and Thr119 of human G-substrate provided in SEQ ID NO.: 1). In other preferred embodiments, the G-substrate fragment contains the consensus phosphorylation sequence PRRKDTPA (SEQ ID NO. 4), corresponding to amino acids 67-74 and 118-125 of SEQ ID NO.: 3 (amino acids 63-70 and 114-121 of SEQ ID NO.: 1). Suitable G-substrate fragments contain at least 10, 15, 20, 25, 30, 35, 40, 45, 50, 60, 70, 80, 90, 100, or more amino acids. G-substrate fragments include, for example, fragments corresponding to amino acids 7-79; 7-101; 7-142; 23-79; 23-101; 23-142; 79-142; and 101-142 of SEQ ID NO: 1.

G-substrate biological activities include, for example, the ability to inhibit protein phosphatase-1 (PP-1) or PP2A. Preferably, G-substrate fragments are capable of inhibiting PP-1 and/or PP2A with an IC50 of less than about 1 µM, 500 nM, 200 nM, 100 nM, 50 nM, 25 nM, 10 nM, or 1 nM. Exemplary assays for determining the inhibitory effect of G-substrate on PP-1 and PP2A are described by Endo et al. (Neurosci. Res., 43: 79-89, 2003).

By "treating" is meant administering a pharmaceutical composition for the purpose of improving the condition of a patient by reducing, alleviating, or reversing at least one adverse effect or symptom.

By "preventing" is meant identifying a subject (i.e., a patient) having an increased susceptibility to PD but not yet exhibiting symptoms of the disease and administering a therapy according to the principles of this disclosure. The preventive therapy is designed to reduce the likelihood that the susceptible subject will later become symptomatic or that the disease will be delay in onset or progress more slowly than it would in the absence of the preventive therapy.

By a "therapeutically effective amount" is meant a quantity of compound (e.g., a G-substrate protein or an inhibitor of PP2A) delivered with sufficient frequency to provide a medical benefit to the patient. Thus, a therapeutically effective amount of a protein is an amount sufficient to treat or ameliorate a symptom of PD.

By a "vector" is meant a non-chromosomal nucleic acid comprising an intact replicon such that the vector may be replicated when placed within a cell, for example by a process of transformation. Vectors may be viral or non-viral. Viral vectors include retroviruses, adenoviruses, herpesvirus, papovirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

By a "promoter" is meant a nucleic acid sequence sufficient to direct transcription of a gene. Also included in the invention are those promoter elements which are sufficient to render promoter dependent gene expression controllable for cell type specific, tissue specific or inducible by external signals or agents (e.g. enhancers or repressors); such elements may be located in the 5' or 3' regions of the native gene, or within an intron.

By a "neuron-specific promoter" is meant a promoter that results in a higher level of transcription of a gene in cells of neuronal lineage compared to the transcription level observed in cells of a non-neuronal lineage.

By "operably linked" is meant that a nucleic acid molecule and one or more regulatory sequences (e.g., a promoter) are connected in such a way as to permit expression and/or secretion of the product (e.g., a protein) of the nucleic acid molecule when the appropriate molecules (e.g., transcriptional activator proteins) are bound to the regulatory sequences.

By "isolated nucleic acid molecule," or "substantially pure nucleic acid is meant a nucleic acid molecule that is removed from its naturally-occurring position in the human genome. The term includes, for example, a recombinant DNA that is incorporated into a vector or an autonomously replicating plasmid or virus.

By "substantially identical", when referring to a protein or polypeptide, is meant one that has at least 80%, 85%, 90%, 95%, or 99% sequence identify to a reference amino acid sequence. The length of comparison is preferably the full length of the polypeptide or protein, but is generally at least 10, 15, 20, 25, 30, 40, 50, 60, 80, or 100 or more contiguous amino acids. A "substantially identical" nucleic acid is one that has at least 80%, 85%, 90%, 95%, or 99% sequence identify to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

BRIEF DESCRIPTION OF THE DRAWINGS

FIG. 1A is a schematic diagram of a coronal section of rat brain showing the substantia nigra (SN; A9) and the ventral tegmental area (VTA; A10) from which cells were isolated using laser capture microdissection. Dopaminergic neurons are identified in the A9 (FIG. 1B) and A10 (FIG. 1C) by tyrosine hydroxylase immunohistochemistry and shown in various stages of isolation using laser capture microdissection (FIGS. 1D-F). FIG. 1G is a bar graph showing the relative G-substrate mRNA levels (expressed as the ratio of A10 to A9 G-substrate mRNA) in the male mouse (n=3) and human males (n=3) and females (n=4).

FIG. 4A is a bar graph confirming G-substrate knock-down following each of three different siRNA treatments. FIGS. 4B-4D are bar graphs showing the cellular viability of M17 cells following G-substrate knock-down and in response to 6-OHDA, MG-132, and MPP+ treatment, respectively. All data in FIG. 4 are shown as means±SEM (n=6-8) and are representatives of three or more experiments with the similar trends (** is $p<0.001$; n.s. is not significant, One way ANOVA, Tukey test).

FIG. 5A is the amino acid sequence of human G-substrate (SEQ ID NO.: 1). See, for example, Hall et al., 1999; and GenBank Accession No. AAD12588. FIG. 5B is a cDNA encoding human G-substrate (SEQ ID NO.: 2). See, for example, Hall et al., J. Biol. Chem.: 274: 3485-3495, 1999; and GenBank Accession No. AF071789. FIG. 5C is the amino acid sequence of rat G-substrate (SEQ ID NO.: 3). See, for example, Endo et al., Neurosci. Res., 45: 79-89 (2003).

FIG. 6A shows the time course of elevated PP2A activity in control cells following 6-OHDA exposure. FIG. 6B demonstrates that the G-substrate overexpression is capable of reducing PP2A activity below basal levels following 6-OHDA exposure. T123A G-substrate was partially effective; preventing the 6-OHDA-induced increase in PP2A activity. FIG. 6C is a Western blot of immunoprecipitated PP2A from each culture condition demonstrating that the G-substrate effect is not caused by reducing PP2A protein levels. All data in FIG. 6 are shown as means±SEM (n=5; ** is $p<0.005$, two tail t-test).

FIGS. 7A, 7C, 7E, and 7H are Western blots showing phosphorylated and total levels of Akt, GSK3-β, ERK1/2, and p38, respectively, in control and G-substrate-expressing cells following exposure to 50 µM 6-OHDA. FIGS. 7B, 7D, 7F, 7G, and 7I are line graphs showing the densitometric quantification of the Western blots each of the five PP2A substrates. Optical densities of phosphorylated epitopes were normalized with those of total epitopes as an internal control. These values were normalized with optical densities at time t=0 of the control cells. Data are shown as mean±SEM (n=4-5; * is $p<0.05$, Holm-Sidak post-hoc test).

FIG. 8A is a Western blot showing the effectiveness of an Akt siRNA in knocking down Akt levels in M17 cells. FIGS. 8B-8C are bar graphs showing the deleterious effects of reducing endogenous Akt levels on cell survival following 50 µM 6-OHDA exposure. All data in FIG. 7 are shown as means±SEM (n=4; * is $p<0.05$, two tail t-test).

FIG. 10A shows the expression level of VMAT2 protein following transient transfection of either α-synuclein or an unrelated gene (GFP) in M17 cells. FIG. 10B shows the expression level of VMAT2 protein in naïve and α-synuclein overexpressing cells following transfection using a lentiviral vector expressing either G-substrate or an unrelated gene. FIG. 10C shows the expression level of VMAT2 protein following a reduction in G-substrate by RNAi.

FIG. 11A shows that PP2A inhibition using RNAi causes an increase in VMAT2 expression. FIG. 11B shows that pharmacological inhibition of PP2A also increases VMAT2 expression, but does not alter the level of the dopamine transporter (DAT) or tyrosine hydroxylase (TH).

FIGS. 12A-12L are photomicrographs of rat midbrain following dual-labeling fluorescence immunohistochemistry for tyrosine hydroxylase (TH) and G-substrate (G-sub). FIGS. 12B, 12E, 12H, and 12K are photomicrographs of rat midbrain following G-substrate immunohistochemistry. Subjects were either untransduced or overexpressed G-substrate from a lentiviral vector (intra-nigral injection), and were administered either with 21 µg 6-OHDA or vehicle control by intrastriatal injection. FIGS. 12M-12O are photomicrographs of TH immunohistochemistry of the SN of rats administered 6-OHDA and intra-nigral injections of one of an empty lentiviral vector (FIG. 12M), a lentiviral vector containing the control YFP gene (FIG. 12N), or a lentiviral vector expressing G-substrate (FIG. 12O). FIGS. 12P-12Q are bar graphs demonstrating that the G-substrate-containing vector provided significant neuroprotection against 6-OHDA neurotoxicity compared to similar treatment using an empty vector or a vector expressing an unrelated gene. FIGS. 12R-12U demonstrate that G-substrate increases the phosphorylation of Akt, but not the total amount of Akt in the midbrain and striatum of rats. Additionally, G-substrate increased the amount of GSK3β phosphorylation in the striatum.

DETAILED DESCRIPTION

Figure 1:
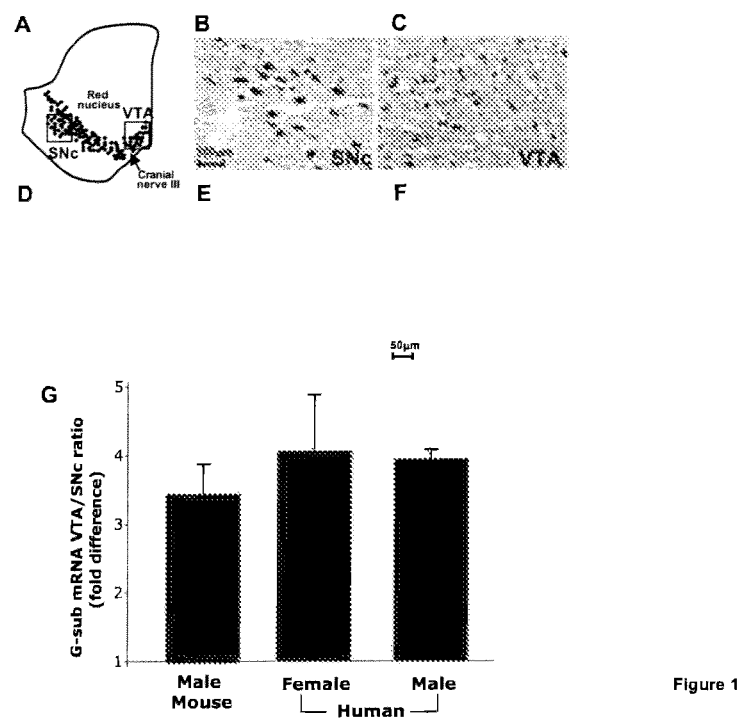
FIG. 1 shows the location of midbrain dopaminergic neurons used for G-substrate assessment.

The methods and compositions of this invention are based on the discovery that an elevated G-substrate level is neuroprotective of dopaminergic neurons. This neuroprotective effect is mediated though an inhibition of protein phosphatase A2 (PP2A) and a concomitant increase in the phosphorylation of Akt and GSK3β. The effectiveness of G-substrate therapy on the survival of dopaminergic neurons was demonstrated both in vitro and in vivo. In vivo experiments using 6-OHDA-lesioned rats indicated that G-substrate levels can be increased in dopaminergic A9 neurons following stereotactic injection of a viral vector encoding G-substrate. The treatment resulted in significant neuroprotection of dopaminergic A9 neurons. Accordingly, Parkinson's Disease (PD), a human disease characterized primarily by a loss of dopaminergic neurons particularly in the A9 midbrain region, can be treated or prevented by increasing the expression or activity of G-substrate, inhibiting PP2A expression or activity, and/or increasing the phosphorylation of Akt, GS3β, or both.

G-Substrate and PP2A

G-substrate was first identified from rabbit cerebellum as an endogenous substrate for the GMP-dependent protein kinase (PKG) (Aswad et al., J. Biol. Chem. 3487-3493; J. Biol. Chem. 3494-3500, 1981) and subsequently shown to be an effective inhibitor of the Ser/Thr phosphatases PP2A and PP1 with similar biochemical properties to DARPP32 (Endo et al., Proc. Natl. Acad. Sci. USA 96: 2467-2472, 1999; Hall et al., J. Biol. Chem. 274, 3485-3495, 1999). However, the function of G-substrate has not previously been characterized in DA neurons. A9 and A10 DA neurons exhibit prominent differences in G-substrate expression with about three fold higher mRNA expression levels in the A10 group (Grimm et al., 2004; Chung et al., 2005).

PP2A is a Ser/Thr phosphatase that is highly expressed in neurons and plays an important role in the regulation of apoptosis by dephosphorylating, and thus altering the activity of key survival molecules (Chatfield et al., Biochem. Biophys. Res. Commun. 323: 1313-1320, 2004; Janssens et al., Biochem. J. 353: 417-439, 2001; Garcia et al., Biochimie 85: 721-726, 2003). Two isoforms of the PP2A regulatory subunit B (B56) were more highly expressed in the vulnerable A9 DA neurons (Chung et al., 2005), indicating that PP2A activity may be elevated in A9 neurons and suggesting that PP2A activity is differentially regulated in A9 and A10 DA neurons.

A prominent target of PP2A is Akt, a regulator of critical biochemical pathways involved in cell survival (Song et al., J. Cell. Mol. Med. 9: 59-71, 2005). Phosphorylation of Ser473 renders Akt active and this site is targeted by PP2A (Song et al., 2005). One of the ways for phosphorylated Akt (pAkt) to mediate its pro-survival effect is by phosphorylating glycogen synthase kinase 3β (GSK3β) at Ser9, inhibiting its pro-apoptotic effects (Chen et al., FASEB J. 18: 1162-1164, 2004). Other known PP2A targets include extracellular signal regulated kinase (Erk) 1 and 2. The relationship of PP2A activity to cell survival is complex, variably pro-apoptotic or anti-apoptotic depending on the molecular target. As with Akt, GSK3β and Erk1/2, dephosphorylation of these targets activates pro-apoptotic signals (Tamura et al., FEBS Lett. 569: 249-255, 2004). In contrast, dephosphorylation of other PP2A targets, including p38 and p53, activates anti-apoptotic signals (Choi et al., J. Biol. Chem. 279: 20451-20460, 2004; Ruano et al., Neurosci. 140: 1157-1168, 2006, Ou et al, Proc. Natl. Acad. Sci. USA 103: 10923-10928, 2006).

Vectors Suitable for Delivery to Humans

This invention features methods and compositions for treating or preventing PD. In one aspect, the invention features methods of gene therapy to express a G-substrate or a PP2A antisense nucleic acid (e.g., an siRNA) in the midbrain, preferably the dopaminergic neurons of the midbrain, of a patient. Gene therapy, including the use of viral vectors as described herein, seeks to transfer new genetic material (e.g., polynucleotides encoding G-substrate) to the cells of a patient with resulting therapeutic benefit to the patient. For in vivo gene therapy, expression vectors encoding the gene of interest is administered directly to the patient. The vectors are taken up by the target cells (e.g., neurons or pluripotent stem cells) and the G-substrate gene expressed. Recent reviews discussing methods and compositions for use in gene therapy include Eck et al., in Goodman & Gilman's The Pharmacological Basis of Therapeutics, Ninth Edition, Hardman et al., eds., McGray-Hill, New York, 1996, Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, and the references cited therein. U.S. Pat. No. 6,080,728 also provides a discussion of a wide variety of gene delivery methods and compositions.

Adenoviruses are able to transfect a wide variety of cell types, including non-dividing cells. There are more than 50 serotypes of adenoviruses that are known in the art, but the most commonly used serotypes for gene therapy are type 2 and type 5. Typically, these viruses are replication-defective; genetically modified to prevent unintended spread of the virus. This is normally achieved through the deletion of the E1 region, deletion of the E1 region along with deletion of either the E2 or E4 region, or deletion of the entire adenovirus genome except the cis-acting inverted terminal repeats and a packaging signal (Gardlik et al., Med Sci Monit. 11: RA110-121, 2005).

Retroviruses are also useful as gene therapy vectors and usually (with the exception of lentiviruses) are not capable of transfecting non-dividing cells. The invention includes use of any appropriate type of retrovirus that is known in the art, including, but not limited to, HIV, SIV, FIV, EIAV, and Moloney Murine Leukaemia Virus (MoMLV). Typically, therapeutically useful retroviruses including deletions of the gag, pol, or env genes.

In another aspect, the invention features the methods of gene therapy that utilize a lentivirus vectors to express G-substrate in a patient. Lentiviruses are a type of retroviruses with the ability to infect both proliferating and quiescent cells. An exemplary lentivirus vector for use in gene therapy is the HIV-1 lentivirus. Previously constructed genetic modifications of lentiviruses include the deletion of all protein encoding genes except those of the gag, pol, and rev genes (Moreau-Gaudry et al., Blood. 98: 2664-2672, 2001).

Adeno-associated virus (AAV) vectors can achieve latent infection of a broad range of cell types, exhibiting the desired characteristic of persistent expression of a therapeutic gene in a patient. The invention includes the use of any appropriate type of adeno-associated virus known in the art including, but not limited to AAV1, AAV2, AAV3, AAV4, AAV5, and AAV6 (Lee et al., Biochem J. 387: 1-15, 2005; U.S. Patent Publication 2006/0204519).

Herpes simplex virus (HSV) replicates in epithelial cells, but is able to stay in a latent state in non-dividing cells such as the midbrain dopaminergic neurons. The gene of interest may be inserted into the LAT region of HSV, which is expressed during latency. Other viruses that have been shown to be useful in gene therapy include parainfluenza viruses, poxviruses, and alphaviruses, including Semliki forest virus, Sinbis virus, and Venezuelan equine encephalitis virus (Kennedy, Brain. 120: 1245-1259, 1997).

Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In vivo DNA-mediated gene transfer into a variety of different target sites has been studied extensively. Naked DNA may be administered using an injection, a gene gun, or electroporation. Naked DNA can provide long-term expression in muscle. See Wolff, et al., Human Mol. Genet., 1:363-369, 1992; Wolff, et al., Science, 247, 1465-1468, 1990. DNA-mediated gene transfer has also been characterized in liver, heart, lung, brain and endothelial cells. See Zhu, et al., Science, 261: 209-211, 1993; Nabel, et al., Science, 244:1342-1344, 1989. DNA for gene transfer also may be used in association with various cationic lipids, polycations and other conjugating substances. See Przybylska et al., J. Gene Med., 6: 85-92, 2004; Svahn, et al., J. Gene Med., 6: S36-S44, 2004.

Methods of gene therapy using cationic liposomes are also well known in the art. Exemplary cationic liposomes for use in this invention are DOTMA, DOPE, DOSPA, DOTAP, DC-Chol, Lipid GL-67™, and EDMPC. These liposomes may be used in vivo or ex vivo to encapsulate a G-substrate vector for delivery into target cells (e.g., neurons or pluripotent stem cells).

Typically, vectors made in accordance with the principles of this disclosure will contain promoters that will cause constitutive expression of the G-substrate coding sequence. Desirably, neuron-specific promoters are used in order to limit or eliminate ectopic G-substrate expression in the event that the vector is incorporated into cells outside of the target region. Several regulatory elements are well known in the art to direct neuronal specific gene expression including, for example, the neural-specific enolase (NSE), and synapsin-1 promoters (Morelli et al. J. Gen. Virol. 80: 571-583, 1999).

Transplantation of Modified Neuronal or Progenitor Cells

In another aspect of the invention, ex vivo gene therapy is used to effect G-substrate expression in the midbrain of a patient. Generally, this therapeutic strategy involves using the expression vectors and techniques described above to transfect cultured cells in vitro prior to implantation of those cells into the brain (i.e., the midbrain) of a patient. The advantage of this strategy is that the clinician can ensure that the cultured cells are expressing suitable levels of G-substrate in a stable and predictable manner prior to implantation. Such preliminary characterization also allows for more precise control over the final dosage of G-substrate that will be expressed by the modified cells.

In one embodiment, autologous cells are isolated, transfected, and implanted into the patient. The use of autologous cells minimizes the likelihood of rejection or other deleterious immunological host reaction. Other useful cell types include, for example, pluripotent stem cells, including umbilical cord blood stem cells, neuronal progenitor cells, fetal mesencephalic cells, embryonic stem cells, and postpartum derived cells (U.S. Patent Application 2006/0233766). In another embodiment, cells are encapsulated in a semipermeable, microporous membrane and transplanted into the patient adjacent to the substantia nigra (WO 97/44065 and U.S. Pat. Nos. 6,027,721; 5,653,975; 5,639,275). The encapsulated cells are modified to express a secreted version of G-substrate which provides therapeutic benefit to the surrounding brain regions.

Synthesis of G-Substrate Proteins

Nucleic acids that encode a G-substrate protein or fragment thereof may be introduced into various cell types or cell-free systems for expression, thereby allowing purification of the G-substrate protein for large-scale production and patient therapy.

Eukaryotic and prokaryotic G-substrate expression systems may be generated in which a G-substrate gene sequence is introduced into a plasmid or other vector, which is then used to transform living cells. Constructs in which the G-substrate cDNA contains the entire open reading frame inserted in the correct orientation into an expression plasmid may be used for protein expression. Prokaryotic and eukaryotic expression systems allow for the G-substrate protein to be recovered, if desired, as fusion proteins or further containing a label useful for detection and/or purification of the G-substrate protein. Typical expression vectors contain promoters that direct the synthesis of large amounts of mRNA corresponding to the inserted G-substrate nucleic acid in the plasmid-bearing cells. They may also include a eukaryotic or prokaryotic origin of replication sequence allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria, such as *Escherichia coli*, requires the insertion of the G-substrate nucleic acid sequence into a bacterial expression vector. Such plasmid vectors contain several elements required for the propagation of the plasmid in bacteria, and for expression of the DNA inserted into the plasmid. Propagation of only plasmid-bearing bacteria is achieved by introducing, into the plasmid, selectable marker-encoding sequences that allow plasmid-bearing bacteria to grow in the presence of otherwise toxic drugs. The plasmid also contains a transcriptional promoter capable of producing large amounts of mRNA from the cloned gene. Such promoters may be (but are not necessarily) inducible promoters that initiate transcription upon induction. The plasmid also preferably contains a polylinker to simplify insertion of the gene in the correct orientation within the vector.

Stable or transient cell line clones of mammalian cells can also be used to express a G-substrate protein. Appropriate cell lines include, for example, COS, HEK293T, CHO, or NIH cell lines.

Once the appropriate expression vectors containing a G-substrate gene, fragment, fusion, or mutant are constructed, they are introduced into an appropriate host cell by transformation techniques, such as, but not limited to, calcium phosphate transfection, DEAE-dextran transfection, electroporation, microinjection, protoplast fusion, or liposome-mediated transfection. The host cells that are transfected with the vectors of this invention may include (but are not limited to) *E. coli* or other bacteria, yeast, fungi, insect cells (using, for example, baculoviral vectors for expression in SF9 insect cells), or cells derived from mice, humans, or other animals. In vitro expression of a G-substrate protein, fusion, polypeptide fragment, or mutant encoded by cloned DNA may also be used. Those skilled in the art of molecular biology will understand that a wide variety of expression systems and purification systems may be used to produce recombinant G-substrate proteins and fragments thereof.

Once a recombinant protein is expressed, it can be isolated from cell lysates using protein purification techniques such as affinity chromatography. Once isolated, the recombinant protein can, if desired, be purified further by e.g., by high performance liquid chromatography (HPLC; e.g., see Fisher, Laboratory Techniques In Biochemistry And Molecular Biology, Work and Burdon, Eds., Elsevier, 1980).

Pharmaceutical Compositions

The present invention includes the administration of G-substrate, biologically active fragments thereof, and other small therapeutic molecules, such as PP2A inhibitors, for the treatment or prevention of PD. The administration of G-substrate, regardless of its method of manufacture, will be in a amount, frequency, and duration sufficient to ameliorate at least one symptom of PD. The symptoms of PD that may be ameliorated include, for example, phenotypic symptoms (e.g., resting tremor) or neuroanatomical symptoms (e.g., protecting or restoring midbrain dopaminergic neurons).

The therapeutic molecules of this invention can be administered to a subject, e.g., a human, alone or in combination with any pharmaceutically acceptable carrier or salt known in the art. Pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. Exemplary pharmaceutically acceptable carriers include physiological saline and artificial cerebrospinal fluid (aCSF). Other physiologically acceptable carriers and their formulations are known to one skilled in the art and described, for example, in Remington: The Science and Practice of Pharmacy, (21st edition), 2005, Lippincott Williams & Wilkins Publishing.

Pharmaceutical formulations of a therapeutically effective amount of a compound of the invention, or pharmaceutically acceptable salt-thereof, can be administered parenterally (e.g. intramuscular, intraperitoneal, intravenous, or subcutaneous injection), or by intrathecal or intracerebroventricular injection in an admixture with a pharmaceutically acceptable carrier adapted for the route of administration.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the proteins of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

The protein or therapeutic compound of the invention can be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or subacute disorder, a treatment with an immediate release form will be preferred over a prolonged release composition. Alternatively, for preventative or long-term treatments, a sustained released composition will generally be preferred.

Example 1

Figure 2:
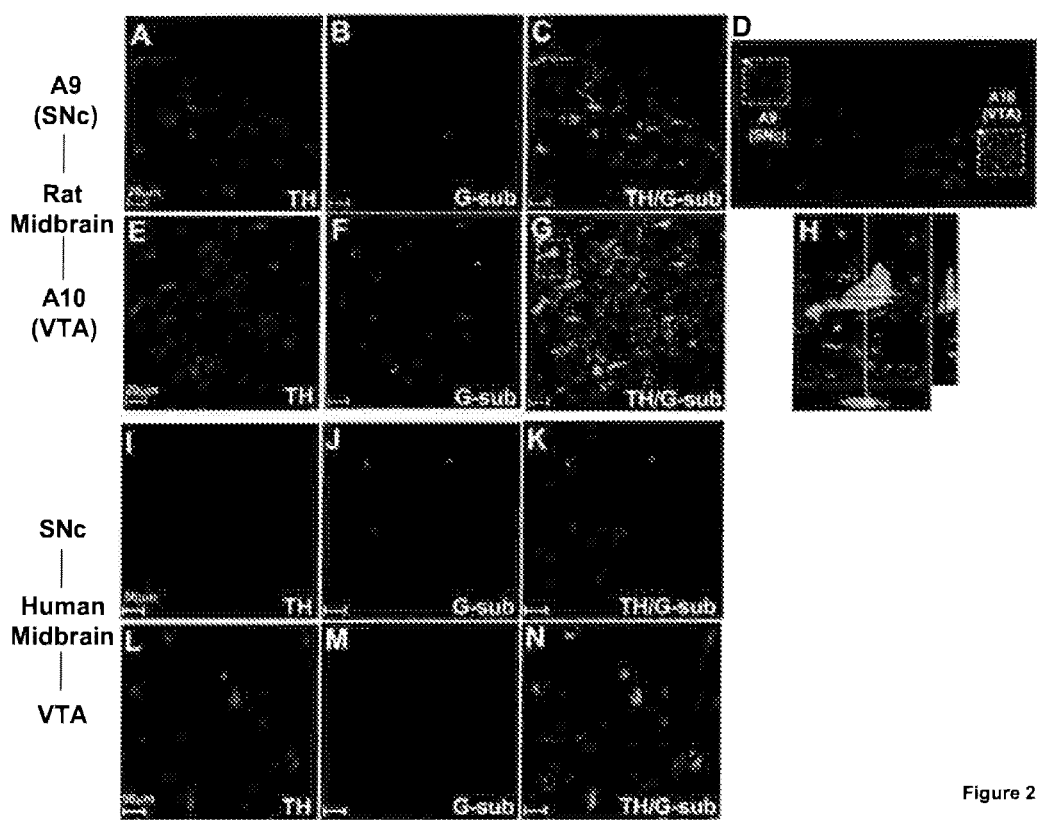
FIGS. 2A-2C, 2E-2G and 2I-2N depict a series of photomicrographs showing co-localization of tyrosine hydroxylase (TH) and G-substrate (G-sub) in the rat and human A9 (SN) and A10 (VTA) midbrain regions using dual-labeling fluorescence immunohistochemistry. Photomicrographs of exemplary dual-labeled tissue sections are shown for each label individually and both labels simultaneously, demonstrating that TH and G-sub co-localize to the same cells having a neuronal morphology.
FIG. 2D is a low power photomicrograph showing the TH distribution in the rat midbrain.
FIG. 2H is a z-stack confocal image of an exemplary midbrain dopaminergic neuron that is positive for both TH and G-substrate.

G-substrate is More Highly Expressed in A10 DA Neurons Compared to A9 DA Neurons Recent microarray studies comparing gene expression profiles of A9 and A10 DA neurons have suggested that G-substrate mRNA is found in higher levels in A10 DA neurons compared to A9 DA neurons in the rat (Grimm, et al., Proc. Natl. Acad. Sci. USA 101: 13891-13896, 2004) and mouse (Chung et al., Hum. Mol. Genet. 14: 1709-1725, 2005). Dopaminergic A9 and A10 neurons were collected from mouse and human midbrain using quick tyrosine hydroxylase (TH) staining followed by laser capture microdissecion as previously described (Chung et al., 2005). Results from quantitative PCR demonstrated that G-substrate mRNA levels are higher in A10 DA neurons compared to A9 DA neurons in both mouse (3.213 fold±0.31) and human (female: 4.03 fold±0.83, male: 3.92 fold±0.14) (FIG. 1). No gender difference in G-substrate mRNA expression was measured in the human midbrain A9 and A10 neurons (FIG. 1). Additionally, G-substrate and TH immunostaining demonstrated that the levels of both proteins are higher in the A10 area (FIGS. 2E-G and 2L-N) compared to the A9 area (FIGS. 2A-C and 2I-K) in both rat and human midbrain. Notably however, G-substrate immunostaining was not exclusive to TH-positive neurons (FIGS. 2C, G, and N).

Tissue Preparation:

Adult C57/B6 mice (Jackson Laboratory, West Grove, Pa.) were anesthetized with intraperitoneal (i.p.) sodium pentobarbital (300 mg/kg) and decapitated. The brain was removed, snap-frozen in dry ice-cooled 2-methylbutane (−60° C.). Fresh frozen human midbrain blocks were obtained from Harvard Brain Tissue Resource Center. Brains were cut using a cryostat with 10 μm (for mouse) or 18 μm (for human) thickness, mounted on LCM slides (Arcturus) and immediately stored at −70° C.

Quick TH Immunostaining and Laser Capture Microdissection (LCM):

A quick TH immunostaining and LCM was performed accordingly to a previously described protocol (Chung, 2005). Briefly, the tissue sections were fixed in cold acetone for 5 minutes, washed with PBS, incubated with rabbit anti-TH (Pel-Freez Biologicals, Rogers, Ark.; 1:25) for 4 min, washed in PBS, and exposed to biotinylated anti-rabbit antibody (Vector Laboratories, Burlingame, Calif.; 1:25) for 4 min. The slides were washed in PBS, incubated in ABC-horseradish peroxidase enzyme complex (Vectastain™, Vector Laboratories) for 4 min and the staining was detected with the substrate, diaminobenzidine (DAB). Sections were subsequently dehydrated in graded ethanol solution (30 sec each in water, 70% ethanol, 95% ethanol, 100% ethanol, and twice for 5 min in xylene). For LCM, the PixCell II System (Arcturus, Mountain View, Calif.) was used to capture approximately 10~200 neurons. RNA was isolated using PicoPure RNA isolation kit (Arcturus, Mountain View, Calif.).

Real-Time PCR Validation:

Real-time PCR was performed according to a previously described protocol (Chung et al., 2005). Briefly, RNA samples from A9 and A10 DA neurons were reverse-transcribed into cDNA using Sensiscript™ reverse transcriptase (Qiagen, Valencia, Calif.) and oligo dT as the primer. PCR reactions were set up in 25 µl reaction volume using SYBR Green PCR Master Mix (Applied Biosystems, Foster City, Calif.) with 250 nM final concentrations of primers. For each primer pairs, triplicates of three to five independently collected A9 and A10 samples were compared to quantify relative gene expression differences between these cells using the $2^{-\Delta\Delta C_T}$ method (Livak et al., Methods 25: 402-408, 2001). Beta-actin was used as an internal control gene.

Example 2

G-Substrate is Protective Against 6-OHDA and MG-132 Toxicity but not MPP+ Toxicity in BE(2)-M17 Cells In order to investigate the role of G-substrate in neuroprotection, the viability of human dopaminergic neuroblastoma BE(2)-M17 cells having different G-substrate status was assessed in response to a variety of neurotoxic insults. Wild-type and mutant (T123A) G-substrate were overexpressed in BE(2)-M17 cells using a lentivirus-mediated gene delivery system. The mutant G-substrate construct harbors a Thr to Ala point mutation at Thr 123 (T123A) (relative to the rat G-substrate sequence of SEQ ID NO.: 3; corresponding to T119A of human G-substrate (SEQ ID NO.: 1), a residue at which G-substrate is phosphorylatd by PKG (Endo, 2003). Phosphorylation of T123 normally increases the inhibitory activity of G-substrate toward Ser/Thr phosphatases, including protein phosphatase 2A (PP2A). Thus, by mutating this residue to Ala, G-substrate partially loses its Ser/Thr phosphatase inhibitory activity (Endo et al., Neurosci. Res. 45: 79-89, 2003).

Figure 3:
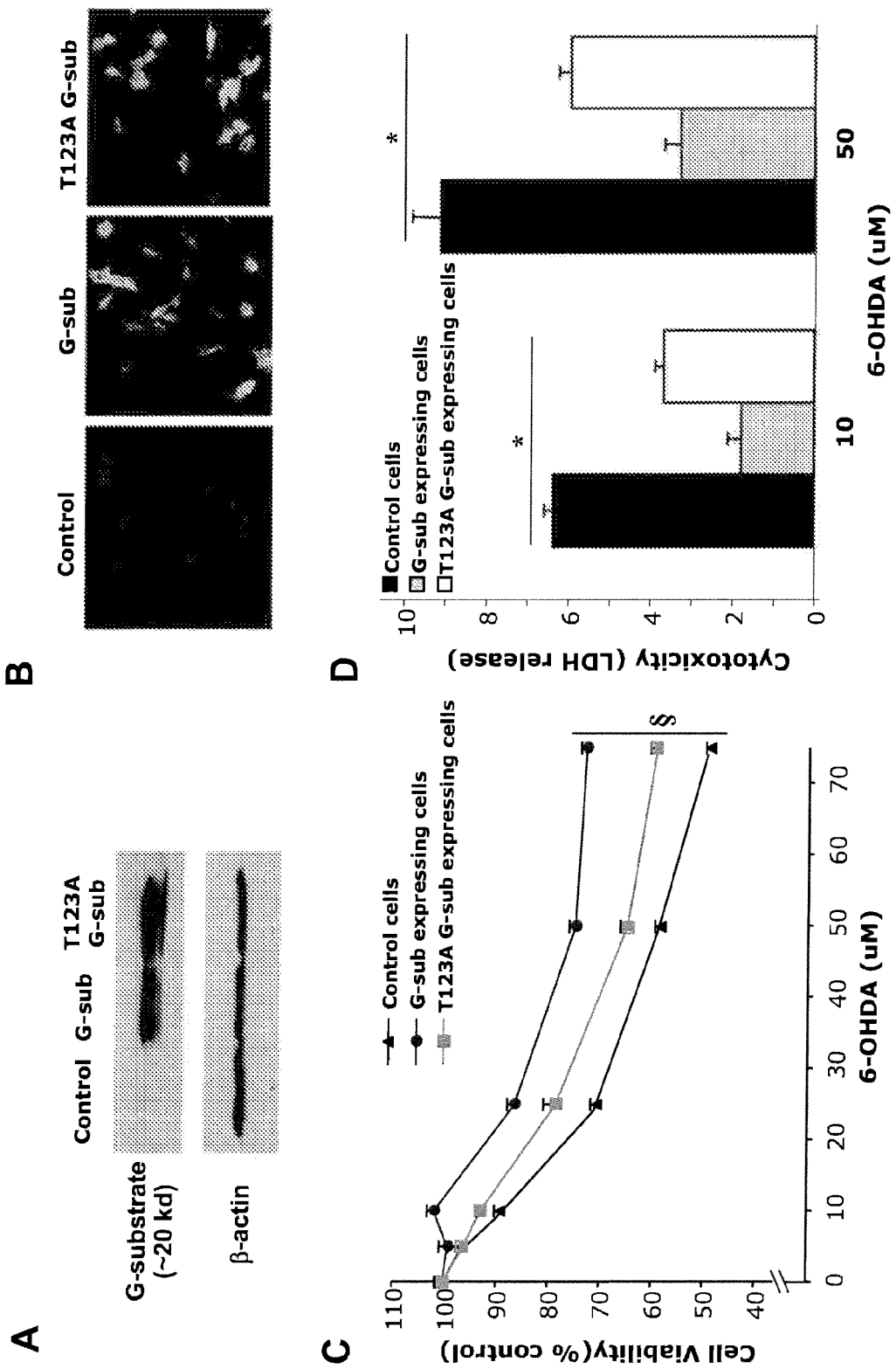
FIG. 3 provides the results of several experiments following the overexpression of wild-type and mutant (T123) G-substrate in BE(2)-M17 cells ("M-17 cells"). Western blotting (FIG. 3A) and immunocytochemistry (FIG. 3B) was used to confirm the overexpression of the wild-type and T123A G-substrate in M17 cells. G-substrate overexpression protected M17 cells against toxicity induced by 6-OHDA (FIGS. 3C-D), MG-132 (FIGS. 3E-F), and MPP+ (FIGS. 3G-H). In each case, the M-17 cell toxicity was assessed by cellular viability and LDH release. All data in FIG. 3 are shown as means±SEM (n=6-8) and are representatives of three or more experiments with the similar trends (§ is $p<0.001$, two way ANOVA; * is $p<0.001$, n.s. is not significant, one way ANOVA, Tukey test).
Figure 3:
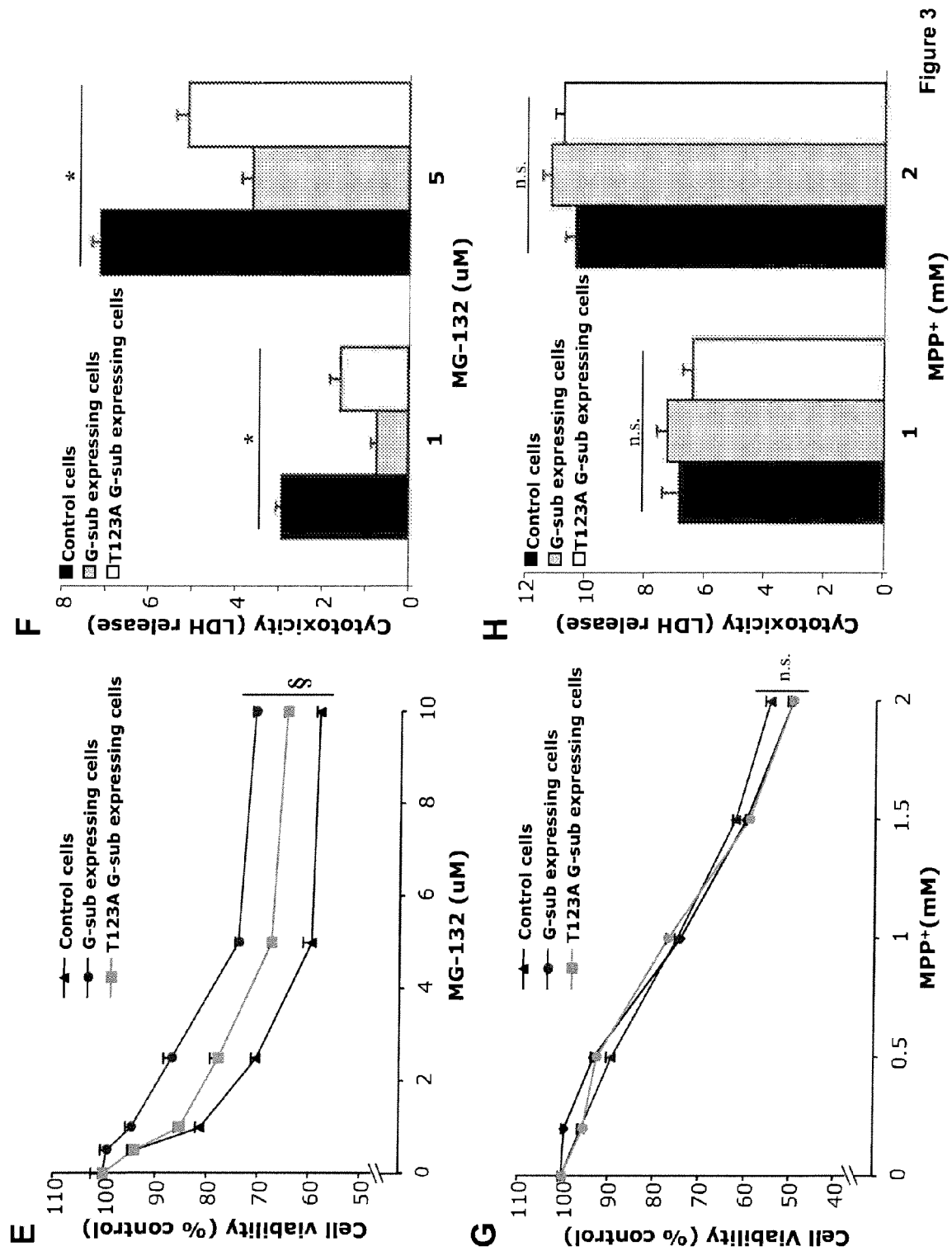

Viability of the M17 cells was assessed following exposure to a variety of neurotoxins, each representing different aspects of PD pathology. 6-hydroxydopamine (6-OHDA) causes oxidative stress. MG-132 induces proteasome inhibition. And, MPP+ causes mitochondrial dysfunction by inhibiting Complex I. Cytotoxicity of M17 cells was determined using both cell viability assays and LDH release. G-substrate overexpression in M17 cells was confirmed by Western blot analysis (FIG. 3A) and by immunocytochemistry (FIG. 3B).

Both wild-type and T123A mutant G-substrate expression were neuroprotective against 6-OHDA and MG-132 compared to control; however, the mutant G-substrate was significantly less effective in its protection compared to the wild-type (FIG. 3C-3F). By contrast, neither wild-type nor T123A mutant G-substrate overexpression was protective against MPP+-induced toxicity (FIGS. 3G-3H).

To further confirm the role of endogenous G-substrate in neuroprotection, the endogenous G-substrate levels were knocked down using siRNA. In a pilot study, three different siRNAs were transiently transfected into BE(2)-M17 cells and G-substrate mRNA levels were measured using quantitative PCR. The siRNA sequences are as follows:

```
siRNA1: GGACUGUGAUCUCAAAAAGTT;      (SEQ ID NO.: 5)

siRNA2: GGGAAAAAAUGUACAGGCCTT;     (SEQ ID NO.: 6)
and siRNA3: GGUCUUUUAUUUCUCCUGUTT.    (SEQ ID NO.: 7)
```

Figure 4:
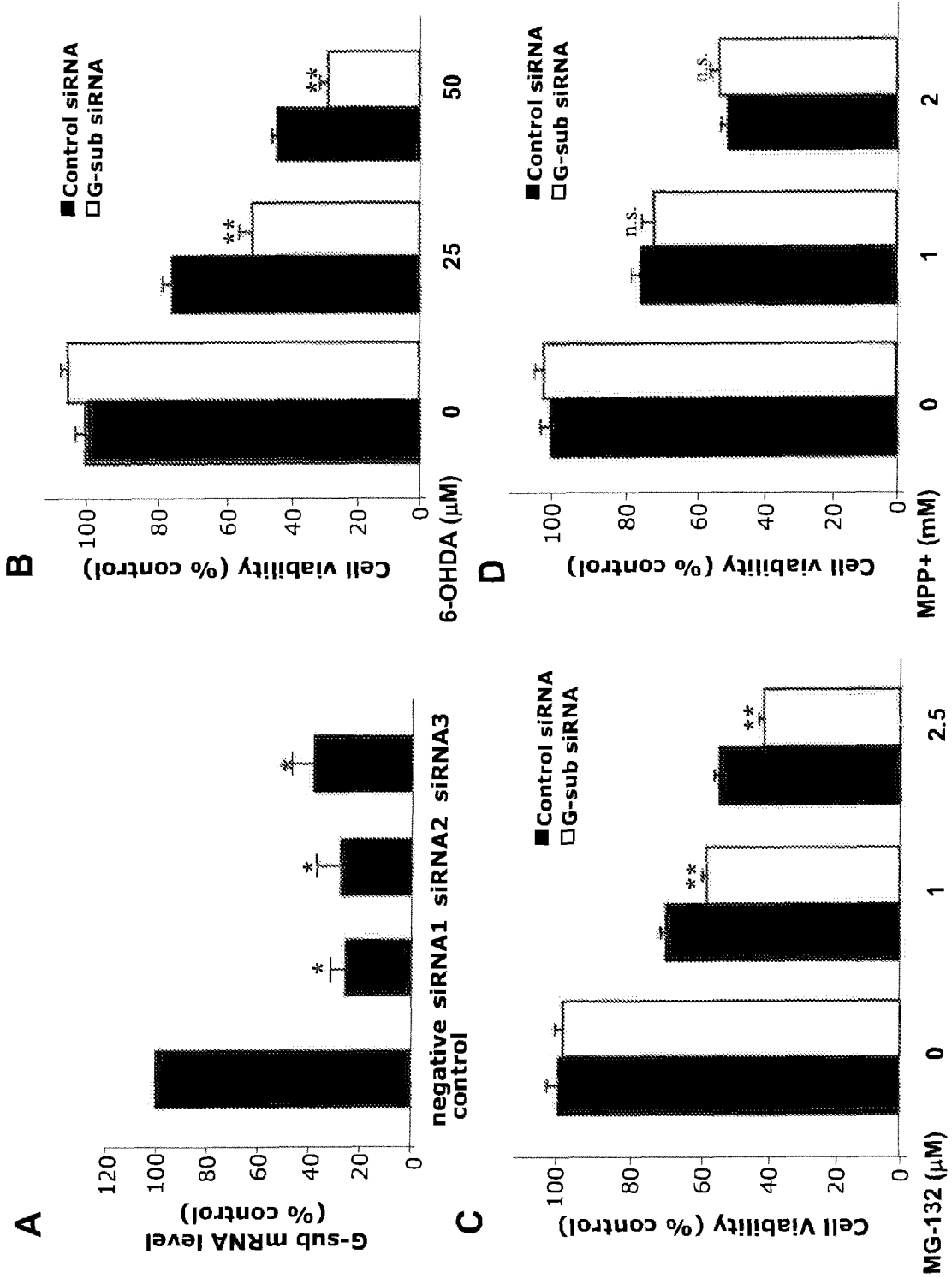
FIG. 4 provides the results of several experiments following G-substrate knock-down using siRNA.

The presence of G-substrate mRNA was clearly detected by quantitative PCR (FIG. 4A), although the G-substrate antibody was not able to detect endogenous G-substrate levels by Western blot analysis (data not shown). All three G-substrate siRNAs significantly reduced endogenous G-substrate mRNA levels (27~38%; FIG. 4A) compared to the control (non-G-substrate) siRNA. Only siRNA1 and siRNA2 were used for subsequent experiments and, because both siRNAs produced similar results, only the results using siRNA1 are shown.

The siRNA-treated cells were exposed to 6-OHDA, MG-132 and MPP+, as described above. M17 cells treated with G-substrate siRNA were significantly more vulnerability to 6-OHDA and MG-132 toxicity compared to those cells transfected with the control siRNA (FIGS. 4B-4C). In further accordance with the observations described above, reduction of endogenous G-substrate mRNA did not affect the sensitivity of M17 cells to MPP+ (FIG. 4D).

These results demonstrate that the inhibitory action of G-substrate on Ser/Thr phosphatases is involved in G-substrate-induced neuroprotection in response to at least molecular pathologies relevant to PD. The fact that G-substrate was not protective against MPP+ toxicity suggests that G-substrate may not overcome cellular damage resulting from mitochondrial dysfunction. It is noteworthy, however, that M17 cells require high doses of MPP+ to induce cytotoxicity compared to other cell types. At such high doses, it is questionable whether the toxicity is caused specifically by Complex I inhibition or by another, non-specific, mechanism. Thus, G-substrate may, in fact, be neuroprotective following mitochondrial insult.

Construction of Lentiviral Vectors:

The human wild type and mutant (T123A) G-substrate cDNAs (FIG. 5) were cloned into the lentiviral vector, pRRL-.cPPT.PGK.W.Sin-18 vector (provided by Drs. R. Zufferey and D. Trono, University of Geneva, Switzerland) and confirmed by sequence analyses.

Production of Lentiviral Vectors and Cell Transduction:

Lower titer lentivirus production for in vitro transdution was based on a previously described protocol (Chung, 2005). Briefly, 293T cells were transfected with four plasmids: pMDLg/pRRE, pMD.G, pRSV.Rev, and pRRL.cPPT.G-substrate.W.Sin-18; (provided by Drs Zufferey and Trono). Virus supernatants were collected and filtered through a 0.2 µm filter and ultracentrifuged to obtain high concentrations of viral stocks. Virus titers were determined according to published protocols (90by) measuring the viral capsid protein p24 by ELISA.

In Vitro Protection Assays:

BE(2)-M17 cells were transduced with lentivirus expressing control or G-substrate with a multiplicity of infection 15. Cells were grown in Optimem™ (Invitrogen, Carlsbad, Calif.) supplemented with 10% heat-inactivated fetal calf serum (Hyclone, Logan, Utah), nonessential amino acid and sodium pyruvate. Cells were maintained at 37° C., in 5% $CO_2$ humid atmosphere. For the bioassay, cells were plated in 96 well plates at 5000 per well. The next day, cells were treated with various concentrations of 6-OHDA (Sigma), MG-132 (Calbiochem) and MPP+ (Sigma) for 20 hrs. The supernatant was used to determine cytotoxicity using LDH release assay kit (Roche, Indianapolis, Ind.) and the cells remaining on the plate was used to determine cell viability using MTS based solution, CellTiter 96 AQueous One™ solution cell proliferation assay (Promega, Madison, Wis.).

siRNA Transfection:

Three different siRNAs for human G-substrate as described herein, a negative control siRNA, and a validated Akt siRNA (Ambion; Austin, Tex.) were used. Cells were plated in 96 well plates at 5000 per well with siRNAs and siPORT NeoFX transfection agent (Ambion, Austin, Tex.). After 48 hrs of incubation with siRNAs, each of the toxicants (6-OHDA, MG-132 or MPP+) were applied to the cells. Cell viability and cytotoxicity was measured after 20 hrs of toxin exposure.

Example 3

G-Substrate Inhibits 6-OHDA-Induced PP2A Activity Increase in BE(2)-M17 Cells

As demonstrated in Example 2, G-substrate-induced protection against 6-OHDA toxicity appears to be mediated through its inhibitory action on Ser/Thr phosphatases. Protein Ser/Thr phosphatases include PP1, PP2A, PP2B, PP2C, PP4, PP5, PP6 and PP7 (Honkanen, 2002). Among these, PP2A is prominently involved in several cellular signal transduction pathways and accounts for a significant fraction of Ser/Thr phosphase activity in neurons (Van Hoof, 2003). It was found that PP1 activity in the absence and presence of 6-OHDA was negligible compared to PP2A activity in BE(2)-M17 cells (data not shown). It is also believed that G-substrate appears to be a stronger inhibitor of PP2A than PP1 (Endo et al., 1999). These is also evidence that PP2A is involved in neuronal response to injury. For example, it has been observed that PP2A activity is elevated following 6-OHDA exposure (Chen et al., FASEB J. 18: 1162-1164, 2004) and over-expression of α-synuclein. Therefore, the following studies focused on PP2A as a potential mediator of G-substrate-dependent protection.

Figure 6:
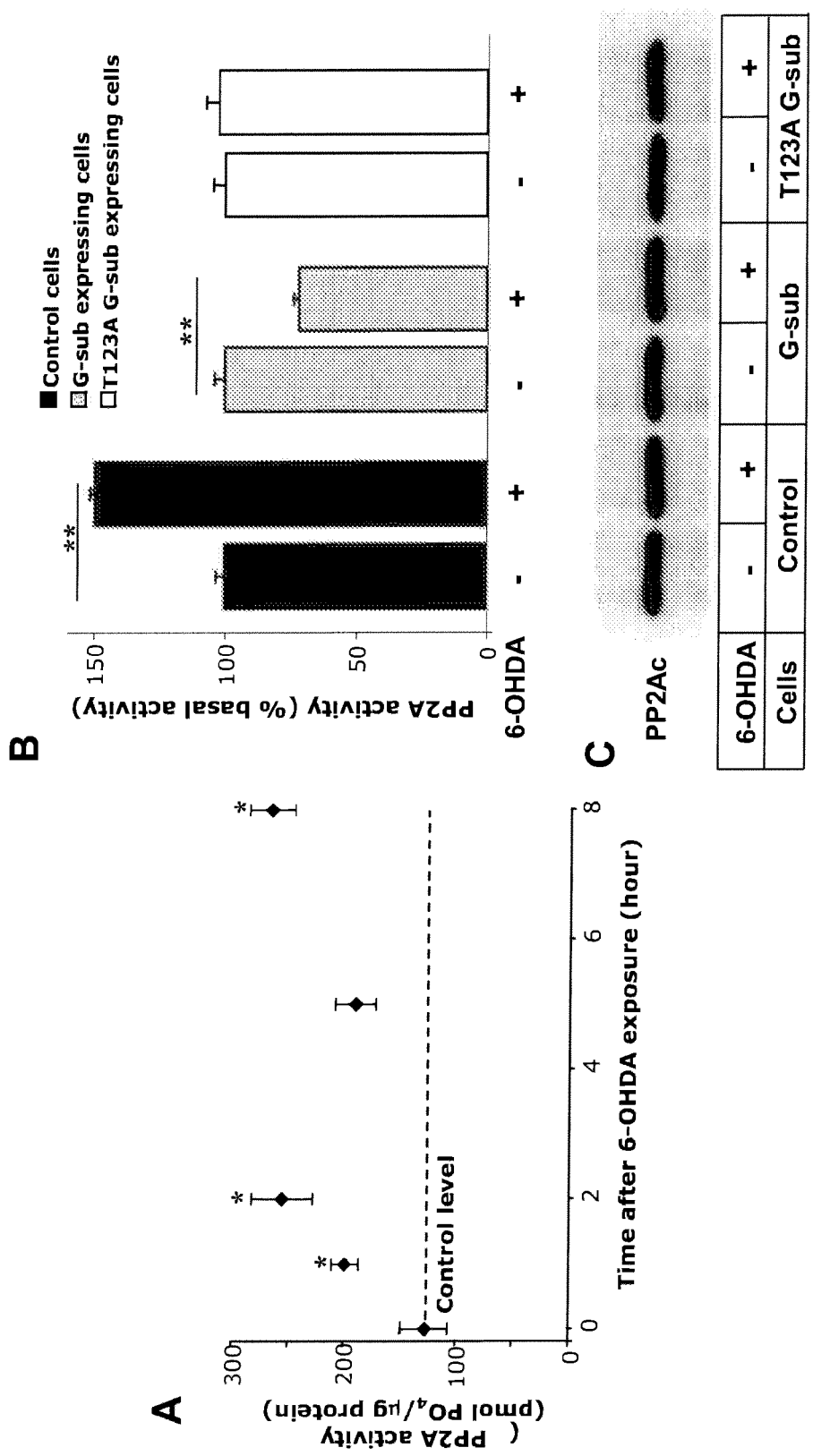
FIG. 6 demonstrates that PP2A activity is elevated in response to a neurotoxic insult, which may be reversed by G-substrate overexpression.

PP2A activity was measured in control BE(2)-M17 cells at various incubation times (t=0, 1, 2, 5 and 8 hr) after exposure to 50 μM 6-OHDA. At all times except t=5 hr, PP2A activity was significantly increased after 6-OHDA exposure compared to basal activity (FIG. 6A). Control, wild-type, and T123A G-substrate-expressing cells were then exposed to 50 μM 6-OHDA for 2 hours before measurement of PP2A activity. Consistent with earlier results, control cells exhibited increased PP2A activity following 6-OHDA exposure. In contrast to control cells, cells overexpressing wild type G-substrate showed a significant reduction in PP2A activity (FIG. 6B). The PP2A activity in T123A G-substrate-expressing cells was also reduced compared to controls, but not reduced as much as observed in the wild-type G-substrate-expressing cells (FIG. 6B). Western blot analysis of immunoprecipitated PP2A indicates that the activity changes measured in these experiments (FIG. 6B) were not attributable to alterations of PP2A protein levels (FIG. 6C). These results, taken together, support the role of PP2A inhibition in mediating the protective effect of G substrate against 6-OHDA-induced toxicity.

PP2A Activity Assay:

PP2A activity was measured using a non-radioactive kit according to the manufacturer's instruction (Upstate Biotechnologies, Lake Placid, N.Y.). After 50 μM 6-OHDA exposure with various times, cells were harvested in 20 mM imidazole-HCl, 2 mM EDTA, 2 mM EGTA, pH7 with a protease inhibitor cocktail (Sigma). Protein concentrations of the lysates were measured using BCA assay (Pierce) and 500 μg of protein was immunoprecipitated using an anti-PP2A catalytic subunit antibody and protein A-Sepharose beads. Immunoprecipitated PP2A was then incubated with phosphopeptide (K-R-pT-I-R-R (SEQ ID NO: 8)) for 10 min at 37° C. Dephosphorylation of the phosphopeptide was assayed spectrophotometrically at 650 nm using Malachite Green.

Example 4

Figure 7:
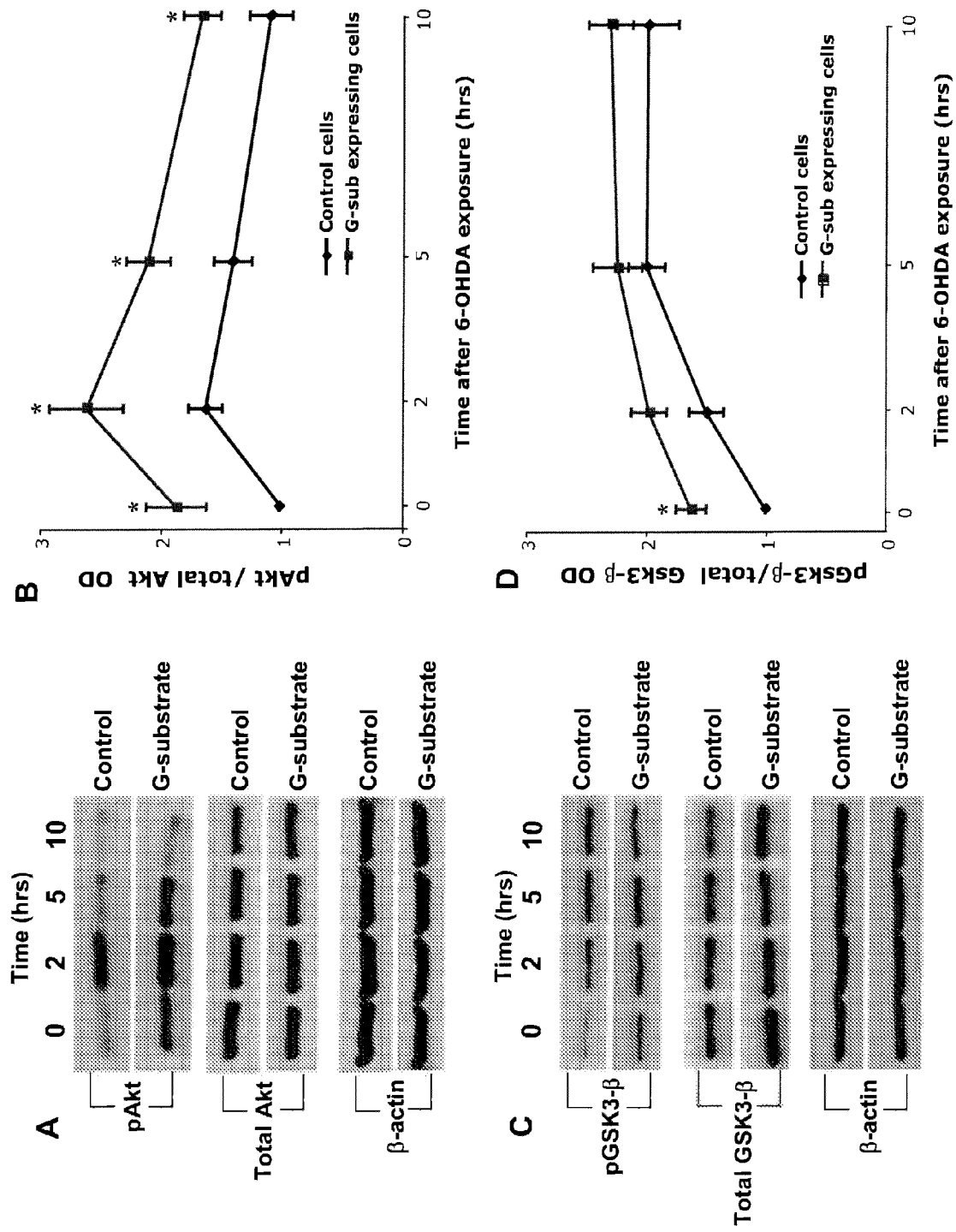
FIG. 7 illustrates phosphorylation changes of known PP2A substrates in response to wild-type and mutant T123A G-substrate expression and 50 µM 6-OHDA exposure.
Figure 7:
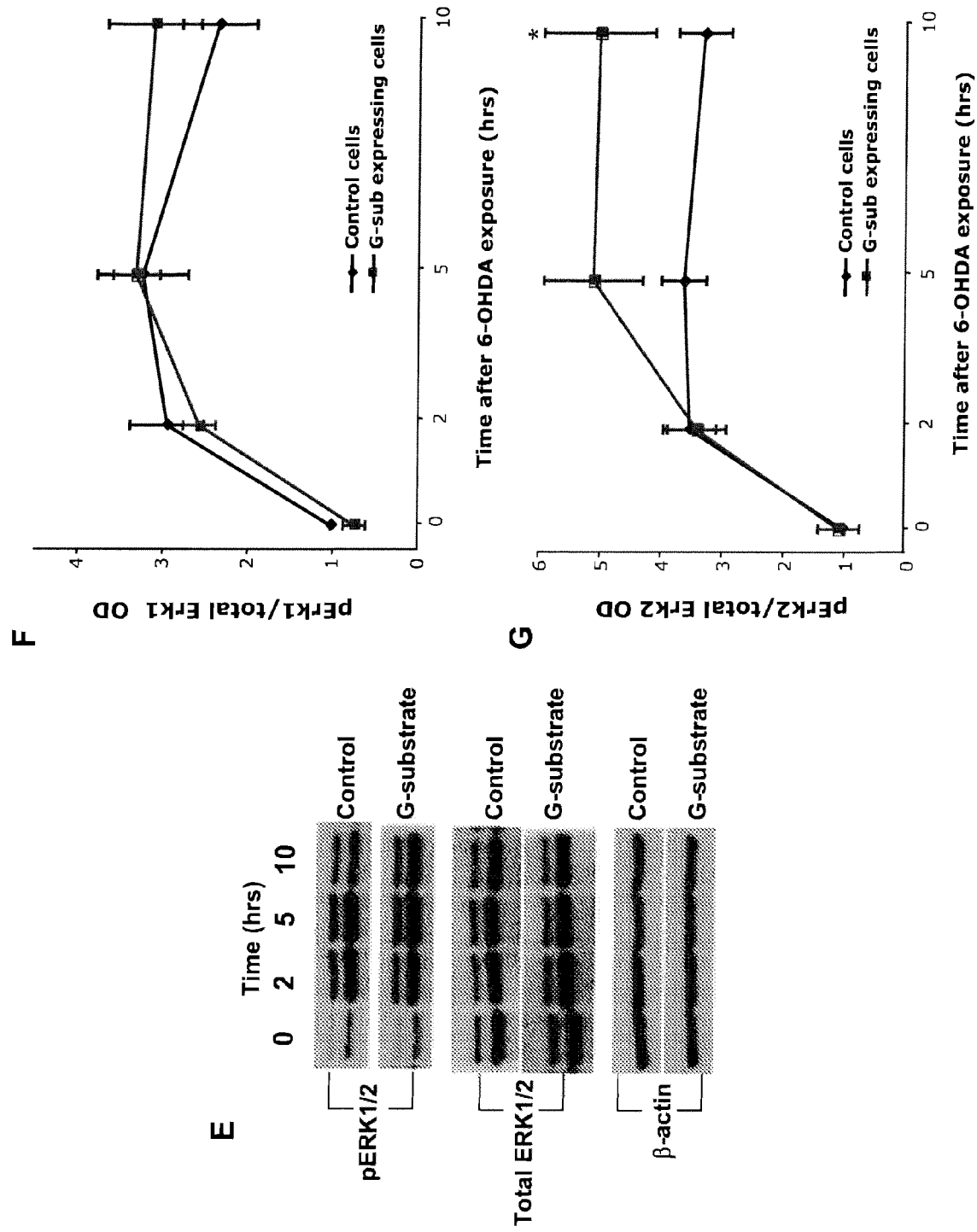
Figure 7:
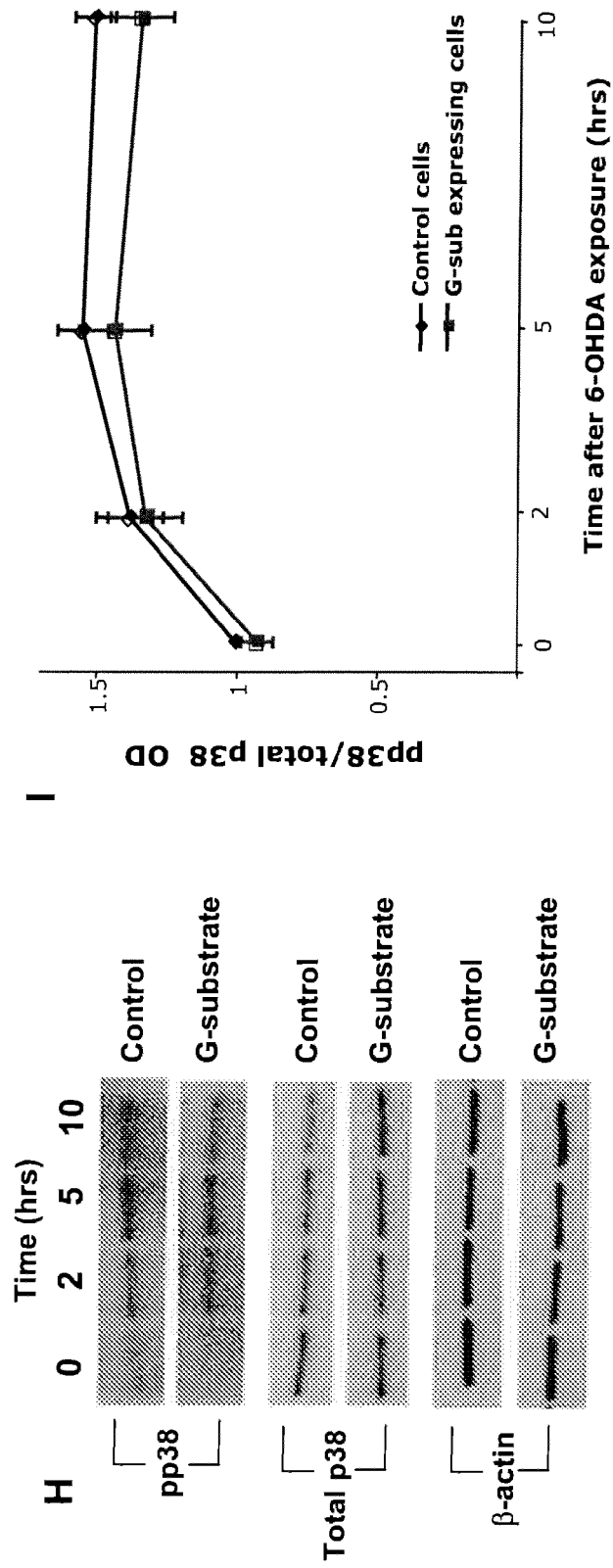

G-Substrate Increases Phosphorylation Levels of PP2A Targets Involved in Cell Survival As described herein, G-substrate overexpression altered the phosphorylation levels of PP2A targets known to play critical roles in cell survival. Akt, GSK3β, and ERK1/2 are known to promote cell survival when phosphorylated (Song et al., J. Cell. Mol. Med. 9: 59-71, 2005; Chen et al., 2004; Ray et al., J. Biol. Chem. 280: 31091-31100, 2005; Tamura et al., FEBS Lett. 569: 249-255, 2004) and phosphorylated p38 is known to mediate cell death in dopaminergic neurons exposed to various toxins including 6-OHDA (Choi et al., J. Biol. Chem. 279: 20451-20460, 2004; Ruano et al., Neurosci. 140: 1157-1168, 2006; Ou et al., Proc. Natl. Acad. Sci. USA 103: 10923-10928, 2006). To test whether changes in phosphorylation levels of these proteins are G-substrate-dependent, both control and G-substrate-expressing cells were exposed to 50 μM 6-OHDA for various durations (t=0, 2, 5 and 10 hr). BE(2)-M17 cells were prepared and cultured as described above. The level of the total and phosphorylated forms of these PP2A substrates was detected by Western blot analysis (FIGS. 7A, 7C, 7E, and 7H). G-substrate overexpression caused a significant increase in basal level of pAkt as well as at 2, 5 and 10 hours following 6-OHDA exposure (FIGS. 7A-7B). The basal level of pGSK3β was also increased in G-substrate-overexpressing cells (FIGS. 7C-7D). The level of pErk2 was increased by G-substrate overexpression only at 10 hours following 6-OHDA exposure in the absence of a basal level increase (FIGS. 7E-7G). pErk1 showed a similar trend as pErk2 but it did not reach the statistical significance (FIGS. 7E-7F). Interestingly, G-substrate overexpression did not alter the level of the pro-apoptotic phosphorylated p38 (FIGS. 7H-7I). Taken together, these data demonstrate that G-substrate significantly modulates certain PP2A substrates known to be important cell survival molecules but does not affect the pro-apoptotic substrate p38.

Example 5

Figure 8:
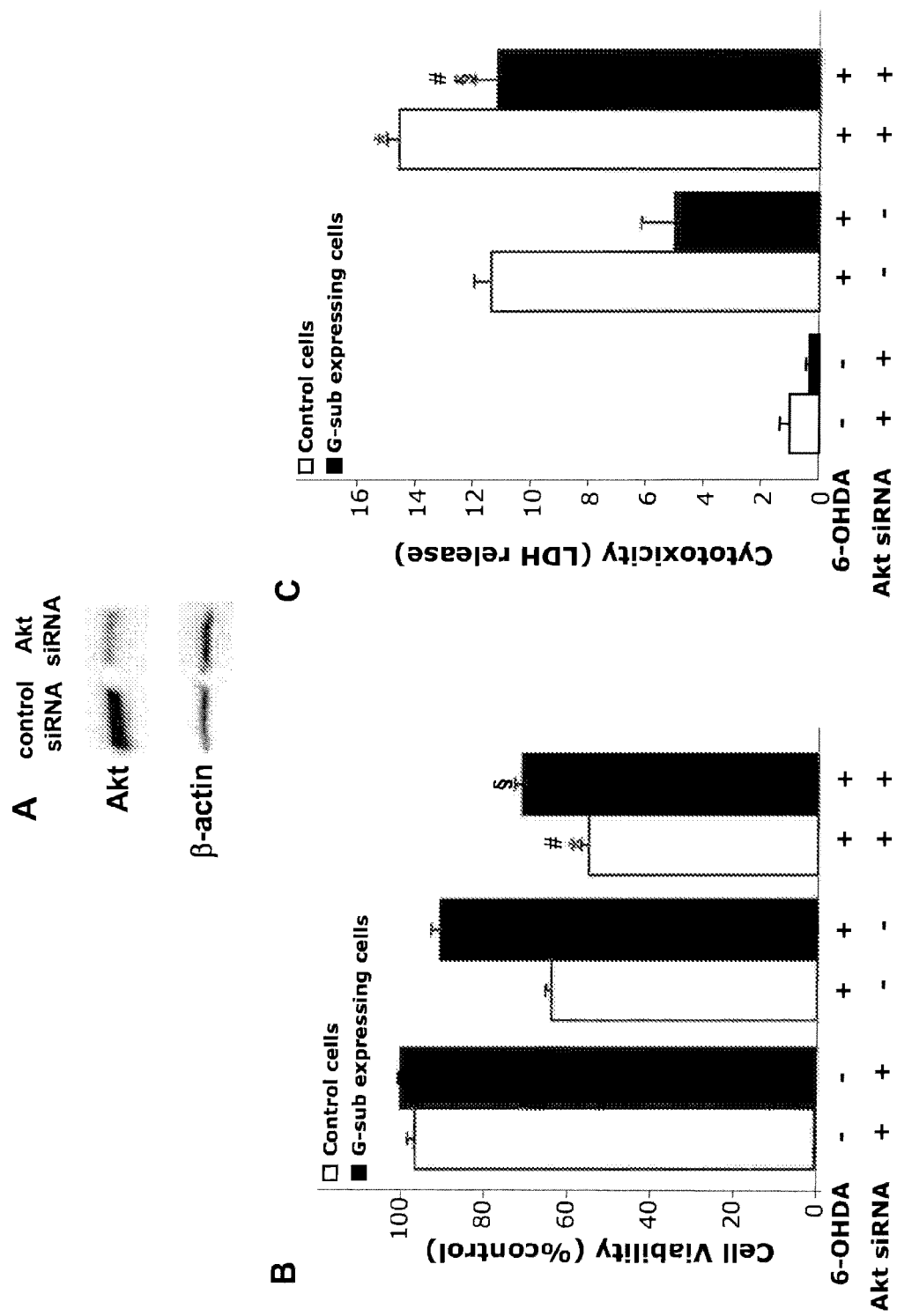
FIG. 8 illustrates the effect of knocking down endogenous Akt levels on G-substrate-mediated neuroprotection.

Knock-Down of Endogenous Akt Decreases G-Substrate-Induced Protection Against 6-OHDA Of the PP2A substrates studied above, only pAkt was significantly increased in G-substrate-overexpressing cells under both basal conditions and following 6-OHDA insult (FIGS. 7A-7B). The endogenous Akt level of control and G-substrate-overexpressing M17 cells was reduced using siRNA. Efficient knock-down of endogenous Akt was confirmed using Western blot analysis (FIG. 8A). Cell viability and cytotoxicity were then measured in the presence or absence of 50 μM 6-OHDA (FIGS. 8B-8C). Knockdown of endogenous Akt resulted in a small increase in 6-OHDAinduced toxicity in control cell lines, as measured by cell viability (FIG. 8B) and cytotoxicity (FIG. 8C). However, the effect on both of these parameters was considerably more pronounced for G-substrate-overexpressing cells for which cell viability was reduced by 39.8±6.7% in the absence of Akt and the 6-OHDA-induced cytotoxicity was significantly increased by 53.2±5.8%. These results demonstrate that Akt is a significant requirement for G-substrate-induced protection against 6-OHDA-induced toxicity.

Example 6

PP2A Inhibition in the Absence of Elevated G-Substrate

Figure 9:
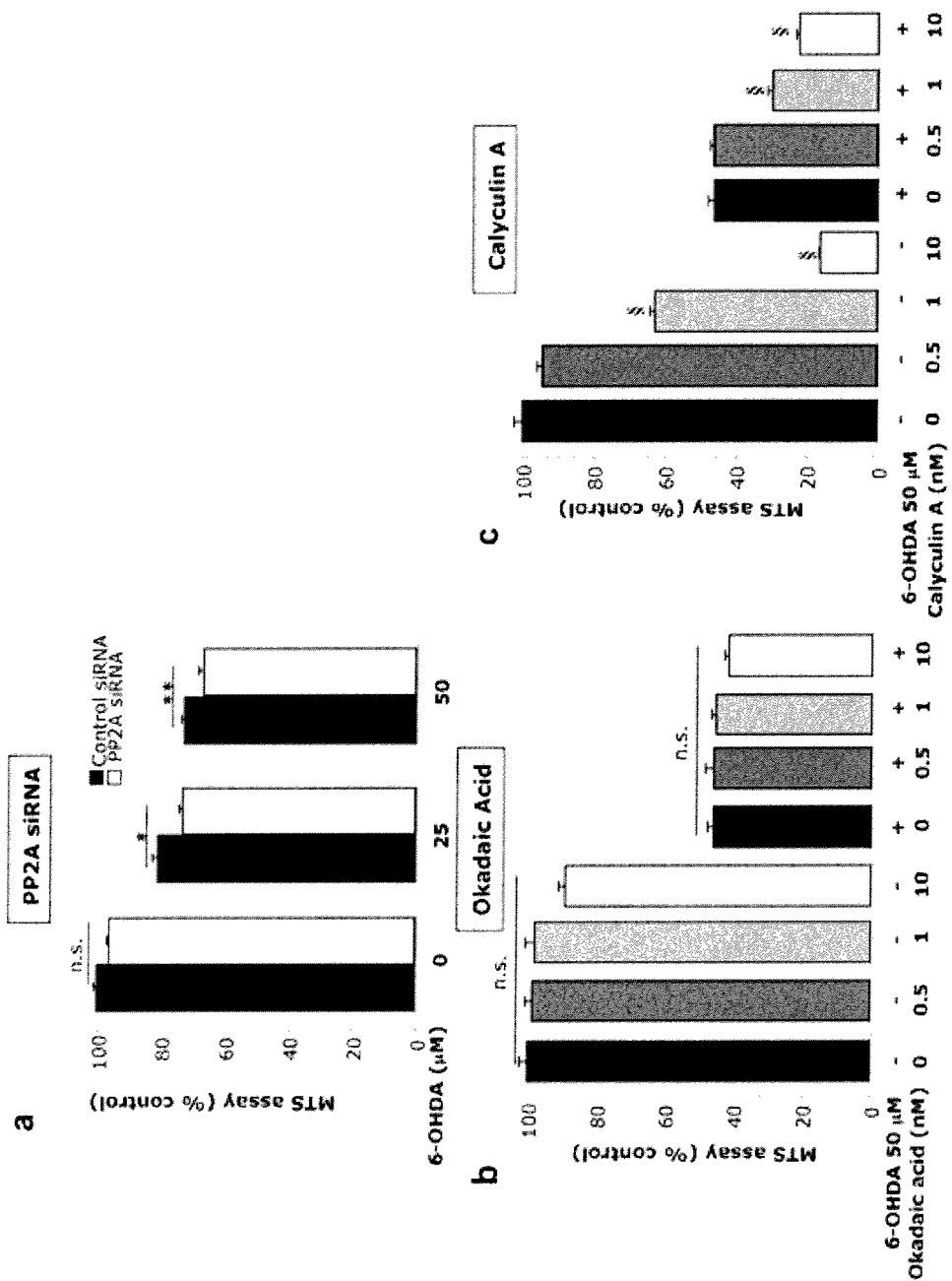
FIG. 9 is a series of bar graphs showing the effect of PP2A inhibition by a PP2A siRNA (FIG. 9A), okadaic acid (FIG. 9B), or calyculin A (FIG. 9C) on neurodegeneration induced by intrastriatal administration of 50 µM 6-OHDA. All data in FIG. 9 are shown as means±SEM (n=6-8; * and § is $p<0.001$, n.s. is not significant by a one-way ANOVA, Tukey test compared to control results for the respective 6-OHDA treatment condition).

The neuroprotective effect of PP2A inhibition following 6-OHDA exposure was investigated in BE(2)-M17 cells. PP2A was inhibited using the chemical inhibitors okadaic acid and calycula A, as well as a PP2A siRNA. Cellular viability was measured using an MTS assay and normalized to control values. As shown in FIG. 9, none of these methods alone were protective against 50 μM 6-OHDA exposure. These results demonstrate that the G-substrate-induced increases in pAkt and/or pGSK3β levels are important factors in the neuroprotective effects observed under conditions of elevated G-substrate.

Example 7

Figure 10:
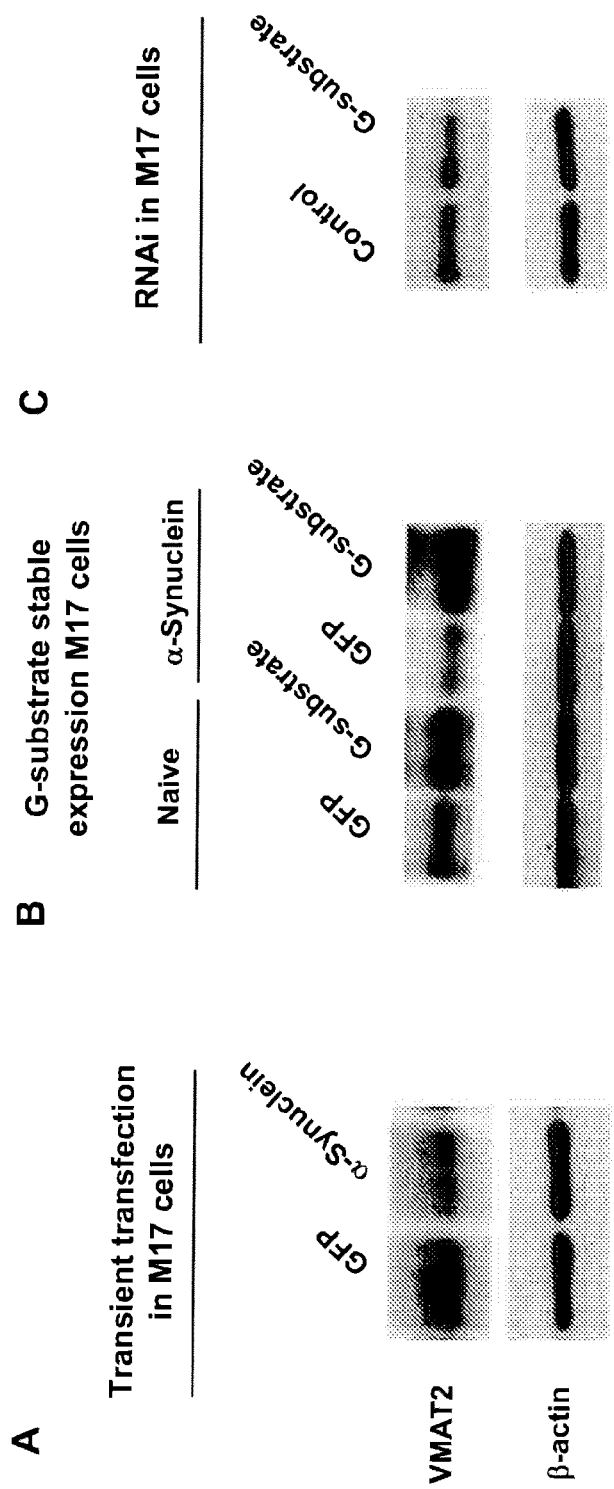
FIG. 10 is a series of Western blots demonstrating the effect of G-substrate on α-synuclein overexpressing cells.

G-Substrate Overexpression Prevents the Loss of Dopaminergic Markers in Cells Overexpressing α-Synuclein BE(2)-M17 cells were used to investigate the interaction between G-substrate and α-synuclein, a known risk factor and possible causative agent in Parkinson's disease. M 17 cells transiently transfected with α-synuclein demonstrated a significant reduction in VMAT2 expression (FIG. 10A), consistent with its known deleterious effects on dopaminergic neurons. G-substrate overexpression in naïve M17 cells (using a lentiviral vector as described above) caused a significant increase in VMAT2 expression (FIG. 10B). Likewise, VMAT2 expression was reduced in naïve M17 cells following the reduction in endogenous G-substrate using siRNA (FIG. 10C).

M17 cells transiently and stably overexpression α-synuclein were transfected using the G-substrate lentiviral vector described above. It was observed that G-substrate was capable of reversing the α-synuclein-induced loss of VMAT2 (FIG. 10B; α-synuclein cells). These data provide additional evidence of the neuroprotective effect of G-substrate on dopaminergic neurons following toxic insults relevant to the etiology of Parkinson's disease.

Example 8

G-Substrate Regulation of VMAT2 is Mediated by PP2A

Figure 11:
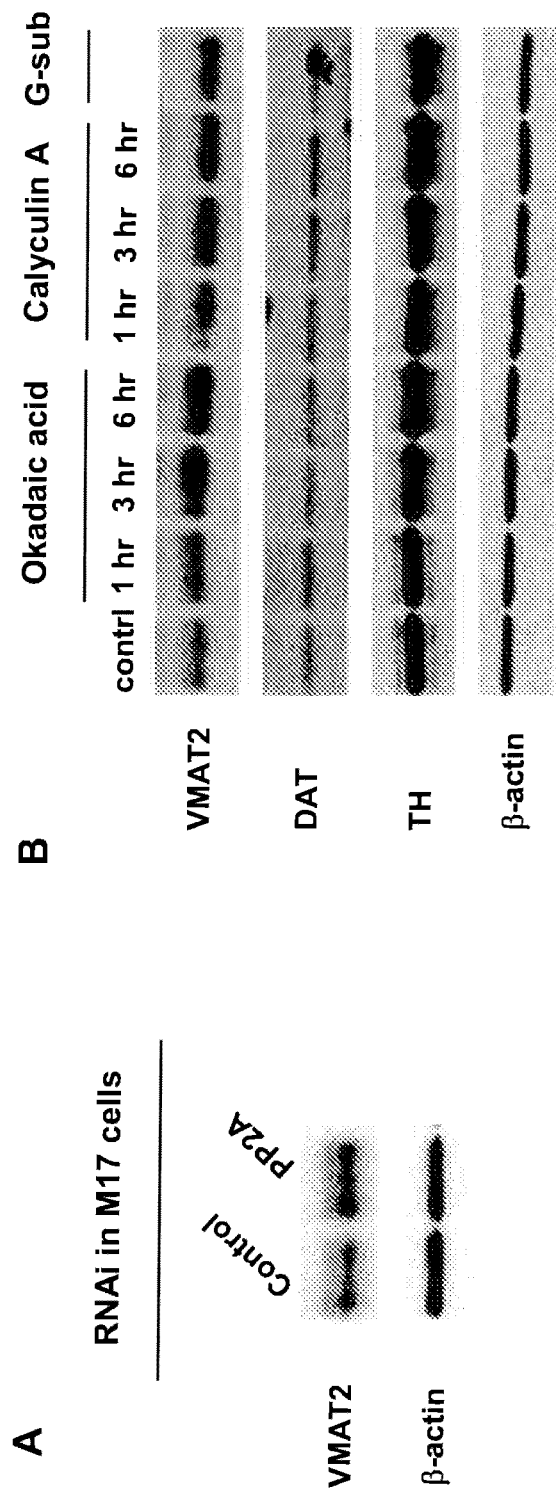
FIG. 11 is a series of Western blots demonstrating that PP2A negatively regulates VMAT2 in M17 cells and the regulation is G-substrate-dependent.

The PP2A regulation of VMAT 2 was investigated in M17 cells. PP2A levels were reduced using RNAi. PP2A reduction caused an increase in VMAT2 levels in naïve M17 cells (FIG. 11A). Furthermore, pharmacological inhibition of PP2A using okadaic acid or calyculin A also resulted in increased VMAT2 levels. The effect of PP2A inhibition was not generalized to other dopaminergic markers tested. As shown in FIG. 11B, PP2A inhibition did not affect expression of the dopamine transporter (DAT) or TH.

Example 9

Lentiviral Delivery of G-Substrate into the Substantia Nigra Protects Midbrain Dopaminergic Neurons in Retrograde 6-OHDA Lesion Model The foregoing results clearly demonstrate that G-substrate provides significant neuroprotection in an in vitro model of dopaminergic neuronal toxicity. As described below, G-substrate overexpression is able to provide similar neuroprotection in vivo in A9 neurons which are the most vulnerable in PD.

Figure 12:
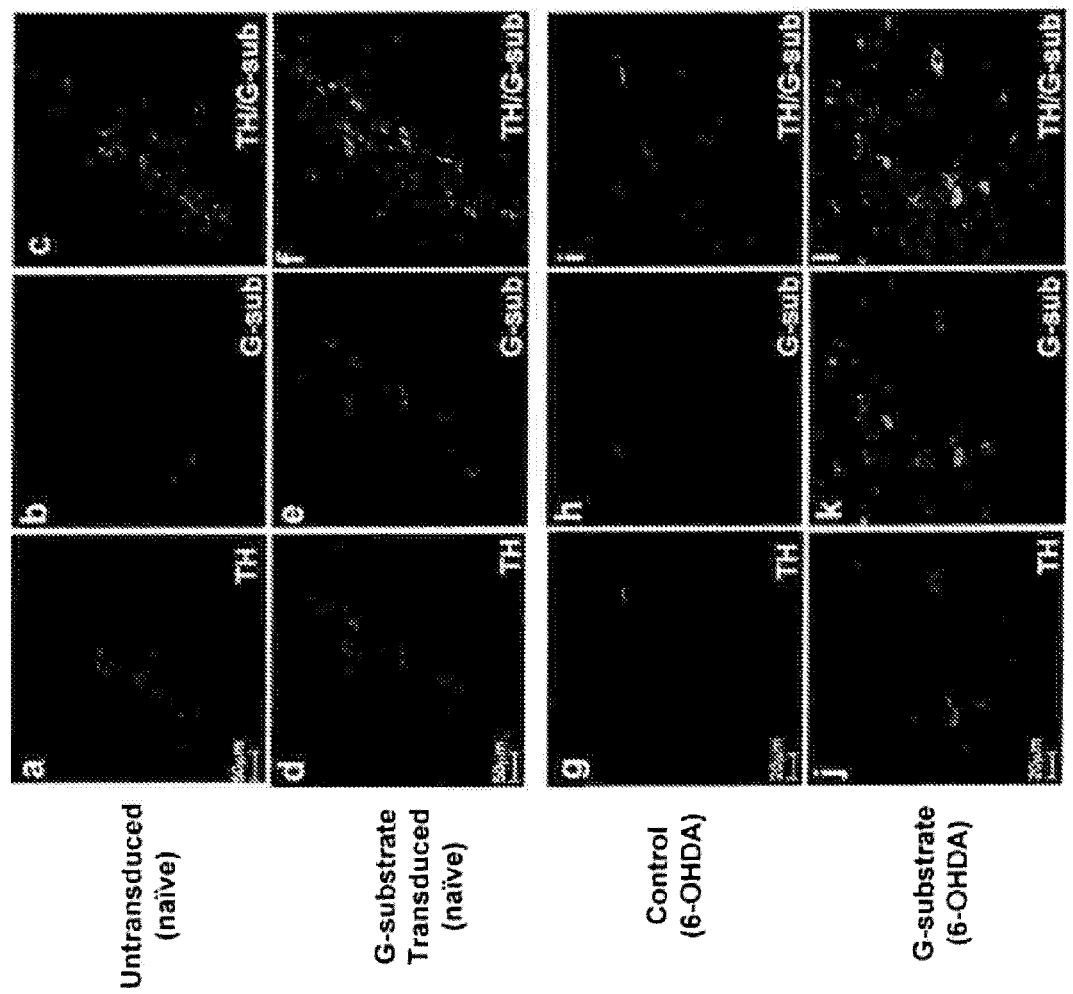
FIG. 12. illustrates the neuroprotective effects of in vivo overexpression of G-substrate.
Figure 12:
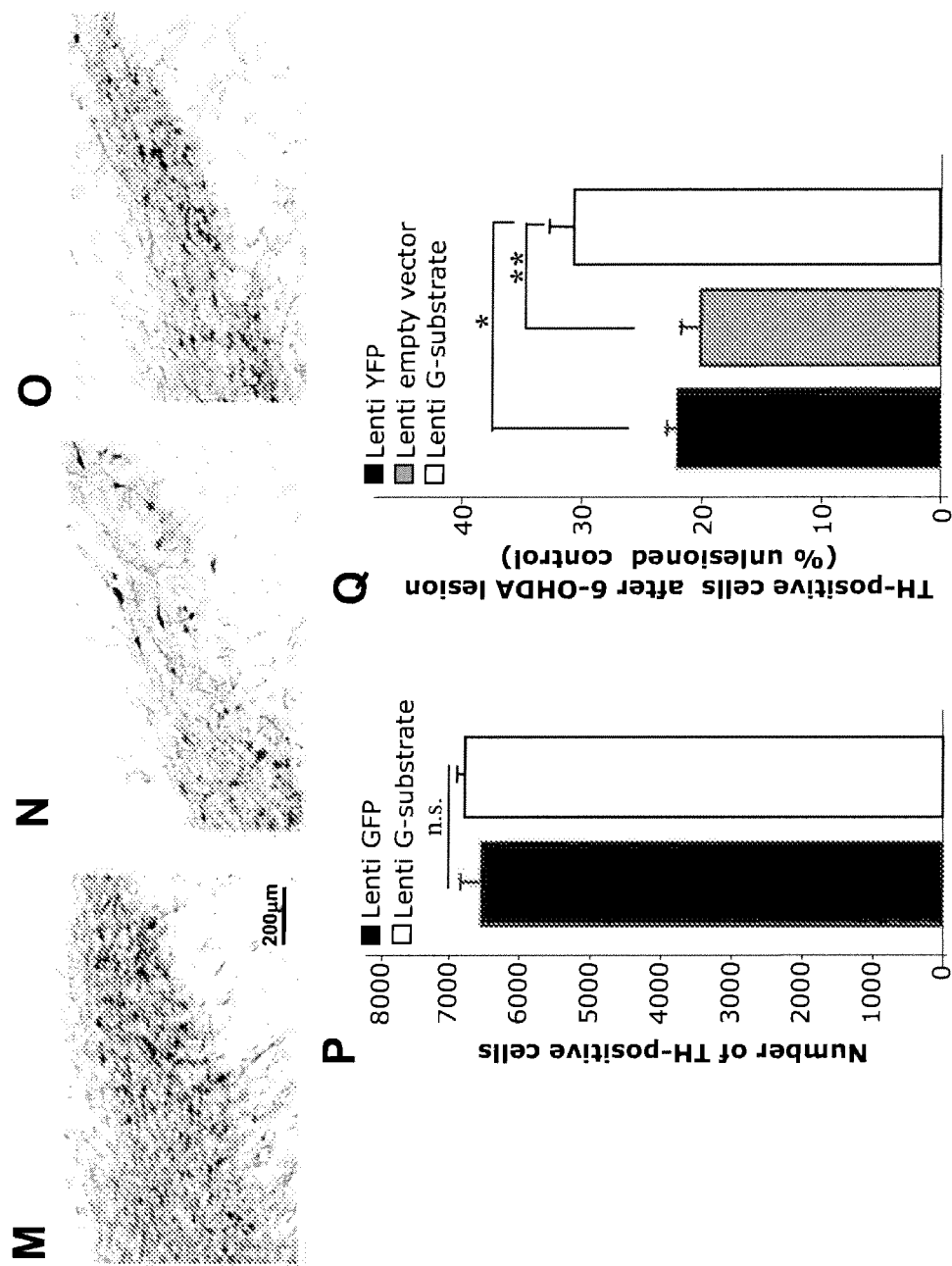
Figure 12:
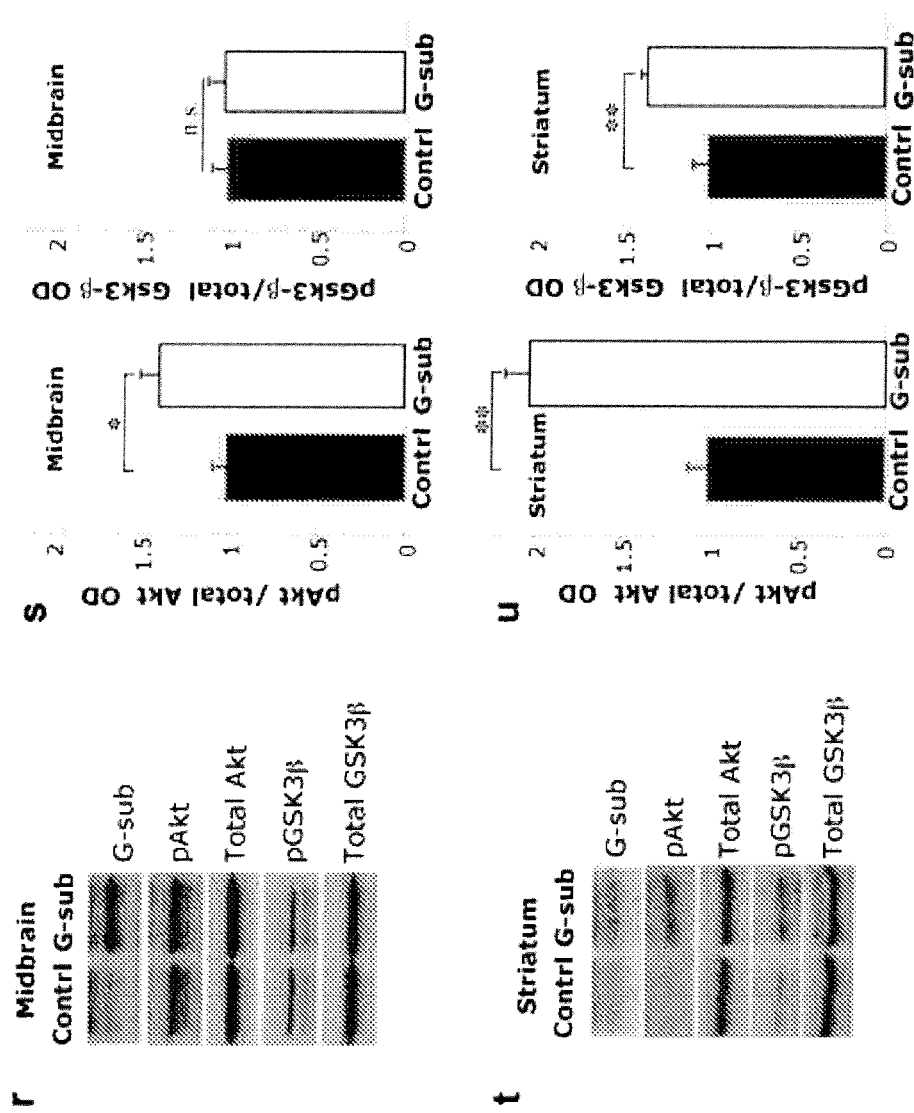

A lentivirus encoding G-substrate (Lenti G-substrate) was stereotactically injected immediately dorsal to the substantia nigra in rats. The transduction efficiency of the lentivirus was then determined. Lenti G-substrate was transduced into TH-positive neurons to varying degrees depending upon the neuroanatomical level. The best transduction efficiency was achieved by injecting the rostral and medial midbrain (16.9-29.3%; FIGS. 12A-12F), whereas very few TH-positive cells were transduced following injections at either caudal or extreme rostral midbrain. On average, 22.3% TH-positive neurons were transduced with lenti G-substrate injections within the rostral and medial midbrain and all the following analyses were focused within these anatomical regions. Importantly, transduction of G-substrate into naïve rats did not alter the total number of TH-positive neurons in midbrain compared to GFP-transduced rats (FIG. 12P).

Retrograde 6-OHDA lesioning within the striatum is a well-established method of creating progressive degeneration of A9 DA neurons. The loss of TH immunoreactivity reflects actual loss of DA neurons (Sauer, 1994).

The in vivo neuroprotective effects of G-substrate against 6-OHDA-induced toxicity was examined by injecting 6-OHDA into the corpus striatum of rats which previously had either G-substrate or control genes (empty vector or YFP) delivered to the midbrain using the lentivirus as described above. 6-OHDA induced approximately an 80% loss of TH-positive neurons in the midbrain (FIG. 12Q) and complete loss of TH immunoreactivity in the striatum (data not shown). The severity of the striatal insult in this paradigm precluded our ability to usefully measure protection of striatal nerve terminals. However, despite the severity of the insult, lenti G-substrate-transduced rats had a significantly higher number of surviving TH-positive neurons than control lentivirus (empty vector) or YFP-injected rats (FIGS. 12M-12O and 12Q). Furthermore, most of the surviving TH-positive neurons in lenti G-substrate-transduced rats were strongly G-substrate-positive (FIGS. 12G-12L). Considering only 22.3% of total TH-positive neurons were transduced with G-substrate, the ~10% DA neuronal protection achieved by G-substrate in vivo indicates that approximately 50% of transduced DA neurons were protected from 6-OHDA-induced toxicity. Thus, these data substantially extend the in vitro findings that an elevated G-substrate level reduces the vulnerability (i.e., is neuroprotective) of A9 DA neurons in vivo.

The in vivo effect of G-substrate overexpression on Akt and GSK3β phosphorylation was investigated. Substantia nigra (FIG. 12R) and striata (FIG. 12T) of the control (empty vector) lentivirus and G-substrate injected were dissected and a Western blot analysis was performed. In accordance with the in vitro results, pAkt levels in G-substrate transduced animals was increased 1.38 fold compared to those injected with control lentivirus (FIGS. 12S and 12U). The level of pGSK3β was unchanged in the SN between the two groups (FIG. 12S) but was modestly but significantly higher in the striatum (FIG. 12U).

Animals:

Female Sprague-Dawley rats weighing ~280 g (Charles River Laboratories) were used in all animal experiments. All rat studies were approved by the McLean Hospital Institutional Animal Care and Use Committee.

Stereotaxic Surgery:

All stereotaxic coordinates were derived from the Rats Atlas of Paxinos and Watson ("The Rat Brain in Stereotaxic Coordinates". Academic Press, San Diego, Calif., 1986). For each surgery animals were deeply anesthetized with ketamine and xylazine (60 mg/kg and 3 mg/kg respectively, i.m.).

Substantia Nigra Lenti Viral Injection:

Rats received two 2.75 µl stereotaxic injections of either lenti-empty vector+lenti-eGFP (n=19), lenti-G substrate+lenti-eGFP (n=19), or lenti-YFP (n=14) and delivered at a rate of 0.2 µl/min using microinfusion pumps (Stoelting Co, Wood Dale, Ill.) with 10 min wait times after each injection. Lenti-eGFP was added to each condition, excluding the YFP condition, to serve as an exogenous marker for surgical targeting (0.5 µl of the total 5.5 µl A volume). SN injection coordinates were as follows: site 1: AP −4.8, ML −2.0, DV −7.2; site 2: AP −5.5, ML −1.8, DV −7.2; and tooth bar set at −3.3. Virus titers (p24) were as follows: G substrate, 60 ng/µl; empty vector, 60 ng/µl; eGFP, 83 ng/µl; and YFP, 60 ng/µl.

6-OHDA Intra-Striatal Injection:

Two weeks following lentiviral injection, animals (lenti-empty vector+lenti-eGFP (n=9), lenti-G substrate+lenti-eGFP (n=9), or lenti-YFP (n=14)) received three 2.5 µl stereotaxic injections of 3.0 µg/µl 6-OHDA (total dose=22.5 µg 6-OHDA) delivered at a rate of 0.5 µl/min and 5 min wait times after each injection. Striatum injection coordinates were as follows: site 1: AP +1.3, ML −2.8, DV −4.5; site 2: AP +0.2, ML, −3.0, DV −5.0; site 3: AP −0.6, ML −4.0, DV −5.5; and tooth bar set at −3.3. The lesion was allowed to progress for 3 weeks after which animals were sacrificed for post mortem analyses.

Perfusions and Tissue Handling:

Animals were deeply anesthetized with an i.p. injection sodium pentobarbital and were sacrificed by exsanguination with the aid of ice-cold saline perfusion. For immunohistochemistry, the brains were then fixed with a 4% paraformaldehyde solution. The brains were then removed from the skull and placed in fresh 4% paraformaldehyde solution for 1 h, and equilibrated through 20% and 30% sucrose solutions and refrigerated until cutting for immunohistochemistry. For immunoblotting, brains injected with lenti-empty vector+lenti-eGFP (n=10) or lenti-G substrate+lenti-eGFP (n=10) were rapidly removed after saline perfusion and sliced coronally using a tissue chopper set to 1 mm (Campden Instruments Ltd., Lafayette, Ind.). On an inverted glass Petri dish over ice, regions of interest (striatum and substantia nigra region) were dissected from the individual 1 mm tissue slices, frozen on dry ice, and stored at −80° C.

Immunohistochemistry:

Brains were cut frozen in the coronal plane at a thickness of 40 µm on a sliding microtome and six series of sections were stored in cryoprotectant. Two full series of sections were processed for visualization of tyrosine hydroxylase (TH) via the biotin-labeled antibody procedure. Briefly, following several washes in a PBS solution containing 0.01% Triton X-100 (PBS-T), endogenous peroxidase was quenched in a 3% hydrogen peroxide solution and background staining was then inhibited in a 5% normal goat serum solution. Tissue was then incubated with rabbit anti-TH antibody overnight (1:5000, Pel-Freez, Rogers, Ariz.). After three washes in PBS-T, sections were sequentially incubated in biotinylated goat anti-rabbit IgG (1:500; Vector, Burlingame, Calif.) for 1 h and the Elite™ avidin-biotin complex (ABC Kits™; Vector, Burlingame, Calif.) for 1 h separated by three washes in PBS. TH immuno staining was visualized following a reaction with 3,3-diaminobenzidine (Vector). Sections were then mounted on glass slides, allowed to dry, dipped into $dH_2O$, dehydrated through graded alcohol (70%, 95%, 100%), cleared in xylenes, and coverslipped with DPX mounting medium. For immunofluorescence staining, sections were washed with PBS-T and blocked with donkey serum. Sections were then incubated with anti-TH (Pel-Freez), anti-G substrate, and anti-eGFP (Chemicon) antibodies overnight and subsequently incubated in the following fluorophore-conjugated secondary antibodies: Alexa 488 (to visualize eGFP), Alexa 568 (to visualize TH), and Alexa 647 (to visualize G-substrate) (Invitrogen, Carlsbad, Calif.). Sections were mounted onto glass slides and visualized using confocal microscopy.

Immunoblotting.

Cells and tissue samples were collected from and suspended in lysis buffer containing: 50 mM Tris-HCl, 0.15 M NaCl, 0.32 M sucrose, 1.0 mM EDTA, and 1% NP-40. In addition, phosphatase inhibitors I and II (1:100) and protease inhibitors (1:100) were added fresh prior to cell lysis (Sigma-Aldrich, P2850, P5276, and P8340 respectively). Following cell lysis, the homogenate was centrifuged, a portion of the supernatant was reserved for protein determination (BCA Assay, Pierce, Rockford, Ill.) and the remaining was stored at −20° C. 20 µg (in vitro cell preps) and 50 µg (tissue dissections) of solubilized protein were mixed 1:1 with sample buffer and boiled for 5 min. The samples and molecular weight standards were separated using the Criterion precast 10% SDS-polyacrylamide gel system (Bio-Rad, Hercules, Calif.). After electrophoresis, the proteins were electrically transferred to PVDF membranes at 100 V for 30 min. After transfer, blots were incubated in Tris-buffered saline with 0.1% Tween 20 (TBS-T) containing 5% BSA. Subsequently, blots were incubated with the following antibodies at 4° C. overnight (1:1000 unless otherwise stated): phospho-Akt (ser473), phospho-GSK3β (ser9), phospho-erk1/2, and phospho-p38 (Cell Signaling Technologies, Danvers, Mass.). HRP-conjugated secondary antibodies were then applied and immunoreactive bands were visualized with chemiluminescence (Amersham Biosciences, Arlington Heights, Ill.) and exposed onto film. Immunoblots were then stripped and re-probed for the expression of the total protein (Cell Signaling) and beta-actin (1:10 000) (Abcam) to serve as a loading control. Optical density analysis (NIH image) was used to determine the relative abundance of protein in each sample. The optical densities of the phospho epitopes were standardized to their respective total proteins and this value was used in the statistical analyses.

Cell Counting:

Estimates of TH-positive neuronal number within the SN were performed using Stereo Investigator™ software (MBF Bioscience, Williston, Vt.) and stereologic principles (West et al., J. Comp. Neurol. 296: 1-22, 1990). The anterior and posterior boundaries of the SN included in the analysis were defined according to the area transduced by lenti-eGFP in preliminary experiments (approximately −4.80 mm through −6.00 mm from Bregma, according to the rat brain atlas of Paxinos and Watson). Stereology was performed using a Zeiss Axiovert microscope (Zeiss, Thornwood, N.Y.) coupled to an Optronics Microfire digital camera (Goleta, Calif.) for visualization of tissue sections. The total number of TH-positive neurons, from tissue sections separated by 120 µm, was estimated from coded slides using the optical fractionator method. For each tissue section analyzed, section thickness was assessed empirically and guard zones of 2 μm thickness were used at the top and bottom of each section. The SN was outlined under low magnification (2.5×) and approximately 50% of the outlined region was analyzed using a systematic random sampling design generated with the following stereologic parameters: grid size, 200×200 μm; counting frame size, 153×140 μm; and dissector height, 16 μm. Neurons were counted under 40× magnification. The coefficients of error (CE) were calculated according to the procedure of Gundersen et al., values <0.10 were accepted.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Other embodiments are within the claims.

What is claimed is:

1. A method for treating Parkinson's Disease in a patient, said method comprising increasing the level of G-substrate in the midbrain dopaminergic neurons of said patient, wherein said method comprises administering to said patient a viral vector comprising a polynucleotide encoding said G-substrate, operably linked to a promoter, wherein neurons in the patient take up the viral vector and express G-substrate.

2. The method of claim 1, wherein said midbrain dopaminergic neurons are located in the substantia nigra A9 region.

3. The method of claim 1, wherein said viral vector is selected from the group consisting of an adenovirus, adeno-associated virus, and retrovirus.

4. The method of claim 1, wherein said viral vector is a lentiviral vector.

5. The method of claim 1, wherein said viral vector is administered to the substantia nigra.

6. The method of claim 1, wherein said viral vector encodes a biologically active fragment of G-substrate comprising the amino acid sequence of SEQ ID NO: 4.

* * * * *

SEQUENCE LISTING

<160> NUMBER OF SEQ ID NOS: 8

<210> SEQ ID NO 1
<211> LENGTH: 155
<212> TYPE: PRT
<213> ORGANISM: Homo sapiens

<400> SEQUENCE: 1

```
Met Met Ser Thr Glu Gln Met Gln Pro Leu Glu Val Ser Glu Asp Arg
1               5                   10                  15

Leu Asp Lys Leu Asp Pro Arg Cys Ser His Leu Asp Asp Leu Ser Asp
            20                  25                  30

Gln Phe Ile Lys Asp Cys Asp Leu Lys Lys Pro Arg Lys Gly Lys
        35                  40                  45

Asn Val Gln Ala Thr Leu Asn Val Glu Ser Asp Gln Lys Lys Pro Arg
    50                  55                  60

Arg Lys Asp Thr Pro Ala Leu His Ile Pro Pro Phe Ile Pro Gly Val
65                  70                  75                  80

Phe Ser Glu His Leu Ile Lys Arg Tyr Asp Val Gln Glu Arg His Pro
                85                  90                  95

Lys Gly Lys Met Ile Pro Val Leu His Asn Thr Asp Leu Glu Gln Lys
            100                 105                 110

Lys Pro Arg Arg Lys Asp Thr Pro Ala Leu His Met Ser Pro Phe Ala
        115                 120                 125

Ala Gly Val Thr Leu Leu Arg Asp Glu Arg Pro Lys Ala Ile Val Glu
    130                 135                 140

Asp Asp Glu Lys Asp Gly Asp Lys Ile Ala Ile
145                 150                 155
```

<210> SEQ ID NO 2
<211> LENGTH: 1690
<212> TYPE: DNA
<213> ORGANISM: Homo sapiens

<400> SEQUENCE: 2

```
ggagggcgct gattgtgctg gagaagaaat acatccaccc accctccttt gatgatgtcc      60
actgagcaaa tgcagccact ggaagtctca gaagacagac tggacaagct agaccctcgt     120
tgcagccact tagatgatct ttcagaccag ttcattaagg actgtgatct caaaagaag      180 cctagaaagg gaaaaatgt acaggccacc ctgaatgttg agtcagacca aaaaaaacca     240
aggaggaaag atacaccggc gctgcacatc ccacctttca taccaggtgt gttttcagaa     300
catttaatta aagatacga tgttcaagag agacatccaa agggcaaaat gatccctgtt     360
cttcataaca ctgacctgga acagaaaaag ccaaggagaa aagacacacc tgccctgcac     420
atgtccccct ttgcagcagg tgtgacattg ctcagggatg agagacccaa agcaatcgtg     480
```

```
gaagatgacg aaaaggatgg tgacaagata gctatttaaa gatagtttcc ctgagaccac    540
ttgtaaatag gttagattgg ttccctgtgg tgacctagaa aaaaaataga cttgtttctg    600
ctctcatttt tgtcatcgtc tgacttgaag attcagacac cttctcccca ggagatgtat    660
gccatcaaat tgccagtcac ctctttgtct ctctcttctt tctgagtatg gtttctattc    720
tgtgttttga atttttattt tctaatgcag tggaaaagaa acagatcatc ctaaatgagg    780
aggtaacagg gaaagcactg gggttcggtt tctgcatctt ctggatcaat tcacggaaca    840
gagatcgtgg attacatggg ctccttcttg gttttgctg ctgggcagga cttgacttag    900
cattatccaa gcaccagtcc aagtgggggtt ccctgttgcc agttagagag gtgagaatgt   960
ttggactcta actcaccgat tgctttgcag acaaaggtct tttatttctc ctgtcctatc   1020
ttaagagtcc aaatgtctct ggtgatgttc ctaagaccct tgtcccagat actctaaatg   1080
tgaatgtatg agctggggga gtcaacccag cccaccatgc gttggctgat gataccagag   1140
gcagagagtc ctggtctgtc tgggaagctt agcaatgtat cttcaaattt attttttgttt  1200 ttaaaaatat ttcttaaaca tgctgtccca acatttgtga gttgtgtcac aagtgagtca   1260
ttatcaatgg tagataaaat atcaatgttt gtgatgaatt tactgtaaaa aaattaaggt   1320
caatgaaagc cattctgtta tttttagcat tctcacttat ttagactcta ttacactttc   1380
ttggatgaga ggggagagtg tggtgttagc tagtgagcag aggtctgtat attgtccttg   1440
ccccagcctg caatctgtgg atgcccaggg gaaggcatac aggcctcatc caccaggcaa   1500
tagacaggag agaggtgaga actattttta gaaggaggaa aagtagatac gcaaattgtc   1560
acaactaaga gtgataattt ggtagctctg tatgtatgct ggttccaact gtttaatccc   1620
ttctgtcttt ctgttctcac aaagatggaa aagatgcaag agcttgccgg aaataaagct   1680
acatctatcc                                                         1690
```

<210> SEQ ID NO 3
<211> LENGTH: 159
<212> TYPE: PRT
<213> ORGANISM: Rattus sp.

<400> SEQUENCE: 3

```
Met Ser Thr Glu Met Met Thr Thr Glu Pro Val Gln Ser Leu Glu Leu
1               5                   10                  15

Ser Glu Asp Ile Leu Asp Lys Leu Asp Pro His Gly Ser His Ser Asp
            20                  25                  30

Asp Leu Ser Asp Gln Phe Ile Lys Asp Cys Asp Leu Lys Lys Lys Pro
        35                  40                  45

Arg Lys Gly Lys Asn Val Gln Ala Thr Leu Asn Val Glu Ser Asp Gln
    50                  55                  60

Lys Lys Pro Arg Arg Lys Asp Thr Pro Ala Leu His Ile Pro Pro Phe
65                  70                  75                  80

Ile Pro Gly Val Ile Ser Glu His Leu Ile Lys Arg Tyr Asp Val Gln
                85                  90                  95

Glu Arg Ile Pro Lys Gly Lys Thr Gly Pro Ala Leu His Asn Thr Asp
            100                 105                 110

Val Glu Gln Lys Arg Pro Arg Arg Lys Asp Thr Pro Ala Phe His Val
        115                 120                 125

Pro Pro Phe Val Ala Gly Leu Thr Leu Leu Glu Asp Glu Gly Thr Gly
    130                 135                 140

Val Ile Met Glu Asp Glu Glu Met Asp Gly Asp Lys Leu Ala Ile
145                 150                 155
```

```
<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus phosphorylation peptide

<400> SEQUENCE: 4

Pro Arg Arg Lys Asp Thr Pro Ala
1               5

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ggacugugau cucaaaaagt t                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
gggaaaaaau guacaggcct t                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
ggucuuuuau uucuccugut t                                             21

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Thr

<400> SEQUENCE: 8

Lys Arg Thr Ile Arg Arg
1               5
```